US010219765B2

(12) United States Patent
Noshi

(10) Patent No.: US 10,219,765 B2
(45) Date of Patent: Mar. 5, 2019

(54) NUCLEAR MEDICINE DIAGNOSTIC APPARATUS AND CONTROL METHOD THEREOF

(71) Applicant: Toshiba Medical Systems Corporation, Otawara-shi (JP)

(72) Inventor: Yasuhiro Noshi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 166 days.

(21) Appl. No.: 15/229,640

(22) Filed: Aug. 5, 2016

(65) Prior Publication Data

US 2017/0042492 A1    Feb. 16, 2017

(30) Foreign Application Priority Data

Aug. 12, 2015   (JP) .................... 2015-159675

(51) Int. Cl.
*A61B 6/00* (2006.01)
*A61B 6/03* (2006.01)
*A61B 6/04* (2006.01)

(52) U.S. Cl.
CPC ............ *A61B 6/4417* (2013.01); *A61B 6/032* (2013.01); *A61B 6/037* (2013.01); *A61B 6/0457* (2013.01); *A61B 6/5205* (2013.01)

(58) Field of Classification Search
CPC ....... A61B 6/4417; A61B 6/032; A61B 6/037; A61B 6/0457; A61B 6/5205
See application file for complete search history.

(56) References Cited

U.S. PATENT DOCUMENTS

| 5,812,984 | A  | * | 9/1998  | Goltra ................... G06F 19/363 600/300 |
| 6,698,590 | B2 | * | 3/2004  | Moore ................. B65D 1/0207 206/459.1 |
| 7,835,496 | B2 | * | 11/2010 | Maschke ................ A61B 6/467 378/62 |
| 8,000,510 | B2 | * | 8/2011  | Boeing .................. A61B 6/482 250/370.08 |
| 8,031,828 | B1 | * | 10/2011 | DeMan ................. G06T 11/005 378/15 |
| 8,705,819 | B2 | * | 4/2014  | Carlsen .................. A61B 6/032 382/128 |

(Continued)

FOREIGN PATENT DOCUMENTS

| JP | 8-154913   | 6/1996  |
| JP | 2005-342511 | 12/2005 |

*Primary Examiner* — David Porta
*Assistant Examiner* — Djura Malevic
(74) *Attorney, Agent, or Firm* — Oblon, McClelland, Maier & Neustadt, L.L.P.

(57) ABSTRACT

A nuclear medicine diagnostic apparatus according to an embodiment includes processing circuitry configured to perform control to execute gamma ray acquisition for main imaging for a subject, and prior acquisition to acquire gamma rays in a plurality of acquisition positions in the subject prior to the main imaging, calculate values of gamma ray acquisition time for respective imaging positions in the main imaging, based on count values of gamma rays acquired in the prior acquisition, and perform control to execute the main imaging, based on the calculated values of the gamma ray acquisition time for the respective imaging positions.

16 Claims, 15 Drawing Sheets

(56) References Cited

U.S. PATENT DOCUMENTS

| | | | |
|---|---|---|---|
| 8,838,506 B2* | 9/2014 | Glaser-Seidnitzer ........................ G01R 33/543 706/12 |
| 9,089,265 B2* | 7/2015 | Halliburton ............ | A61B 6/032 |
| 9,568,578 B2* | 2/2017 | Senegas ................ | G01R 33/543 |
| 9,636,077 B2* | 5/2017 | Braun .................... | A61B 6/545 |
| 9,715,575 B2* | 7/2017 | Cohen-Solal ......... | G06F 19/321 |
| 2002/0010551 A1* | 1/2002 | Wang .................... | A61B 6/481 702/19 |
| 2003/0095144 A1* | 5/2003 | Trevino ................. | A61B 5/055 715/764 |
| 2003/0108149 A1* | 6/2003 | Tsuyuki ................ | A61B 6/032 378/54 |
| 2003/0139944 A1* | 7/2003 | Carlsen ................. | G06F 19/322 705/2 |
| 2003/0161435 A1* | 8/2003 | Ozaki .................... | A61B 6/032 378/4 |
| 2004/0008819 A1* | 1/2004 | Drummond ............ | A61B 6/032 378/162 |
| 2004/0066909 A1* | 4/2004 | Lonn ...................... | A61B 6/032 378/65 |
| 2005/0121505 A1* | 6/2005 | Metz ..................... | G06F 19/323 235/375 |
| 2005/0267348 A1* | 12/2005 | Wollenweber .......... | A61B 6/032 600/407 |
| 2006/0178836 A1* | 8/2006 | Bai ...................... | G06F 19/3437 702/19 |
| 2006/0233296 A1* | 10/2006 | Wakai .................... | A61B 6/032 378/8 |
| 2009/0147215 A1* | 6/2009 | Howell .................. | G02C 11/00 351/158 |
| 2010/0183206 A1* | 7/2010 | Carlsen ................. | A61B 6/032 382/128 |
| 2011/0317806 A1* | 12/2011 | Eusemann ............. | A61B 6/405 378/8 |

\* cited by examiner

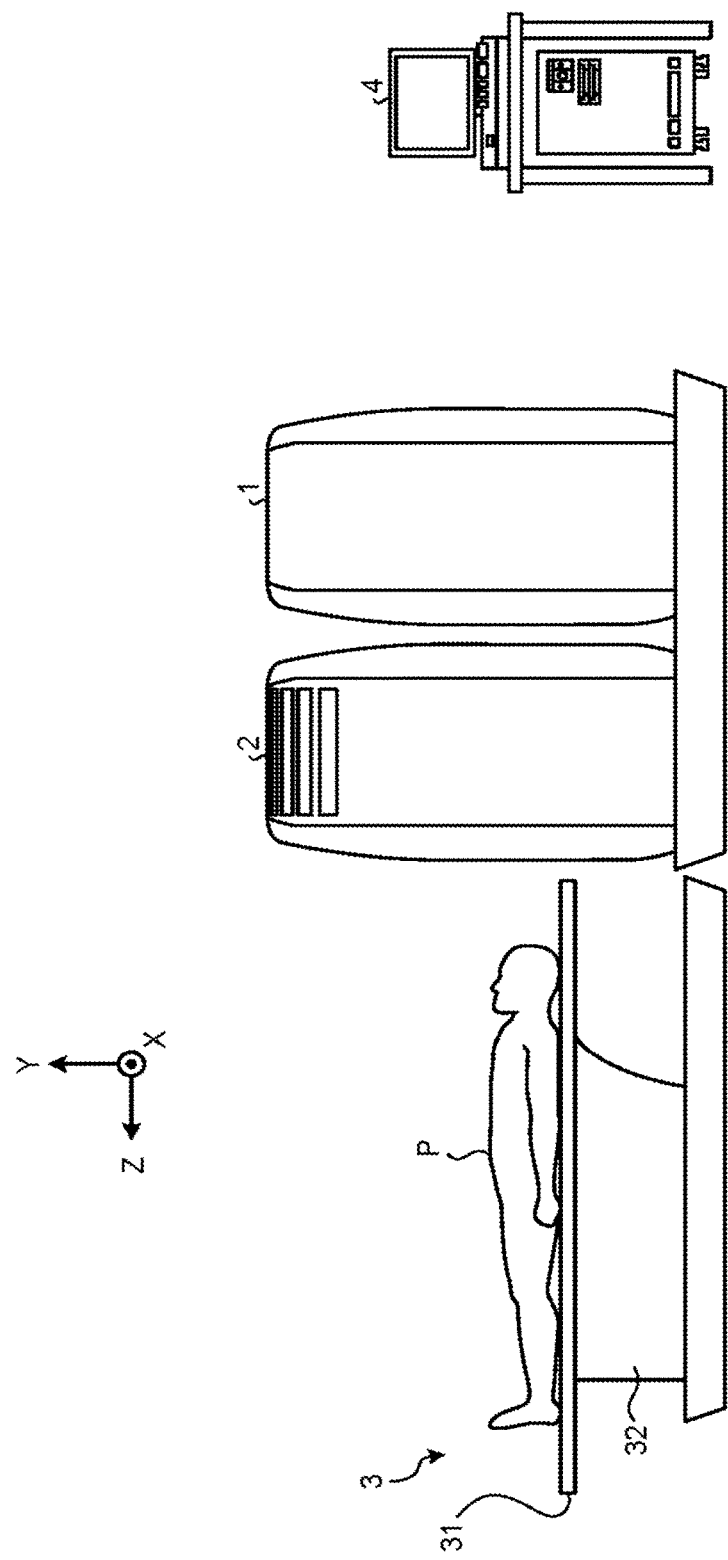

FIG.5A
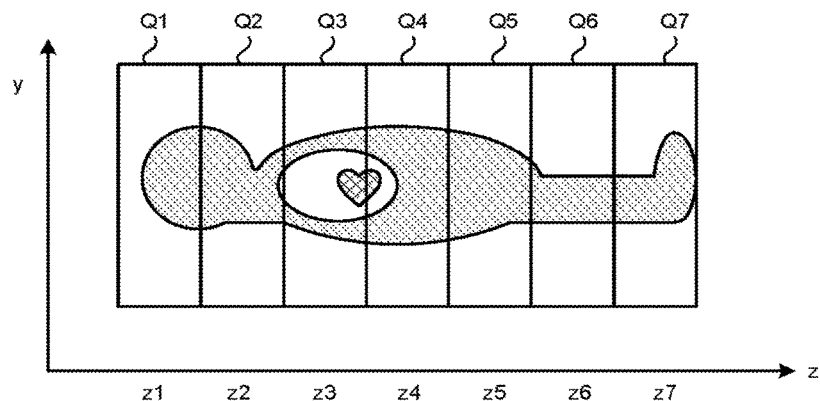
FIG.5B
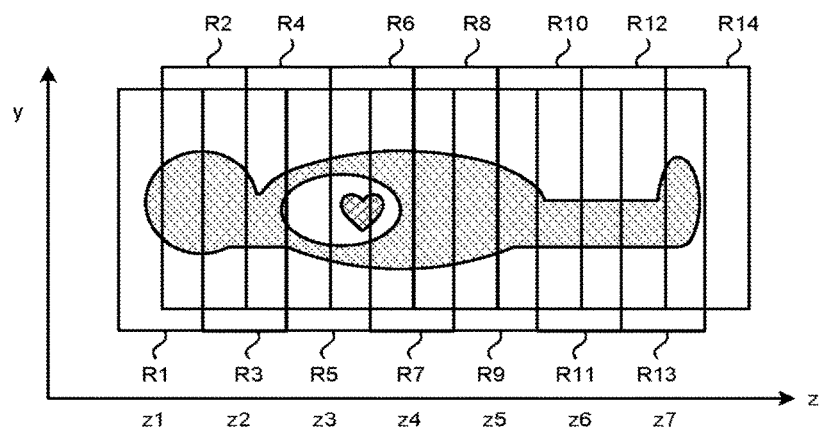
FIG.5C
| z COORDINATE | z1 | | z2 | | z3 | | z4 | | z5 | | z6 | | z7 | |
|---|---|---|---|---|---|---|---|---|---|---|---|---|---|---|
| ACQUISITION POSITION | Q1 | | Q2 | | Q3 | | Q4 | | Q5 | | Q6 | | Q7 | |
| IMAGING POSITION | R1 | R2 | R3 | R4 | R5 | R6 | R7 | R8 | R9 | R10 | R11 | R12 | R13 | R14 |

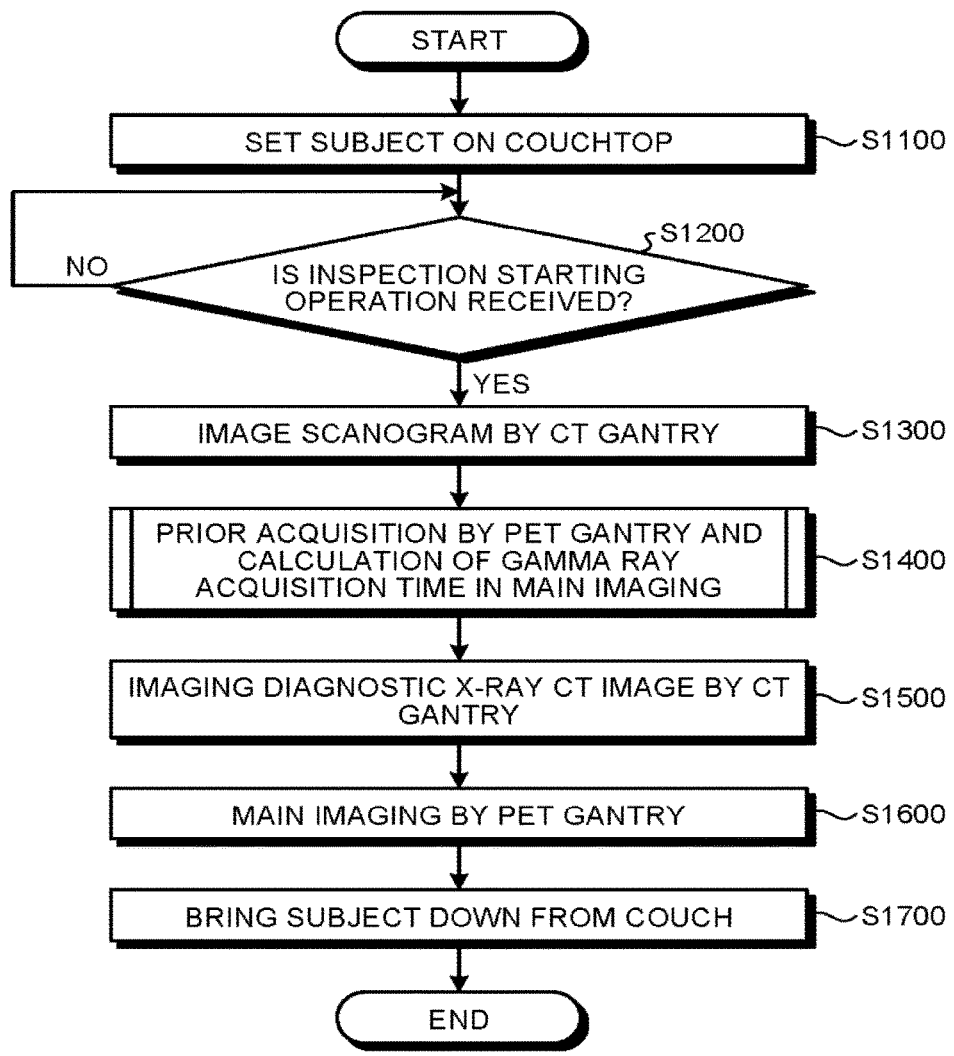

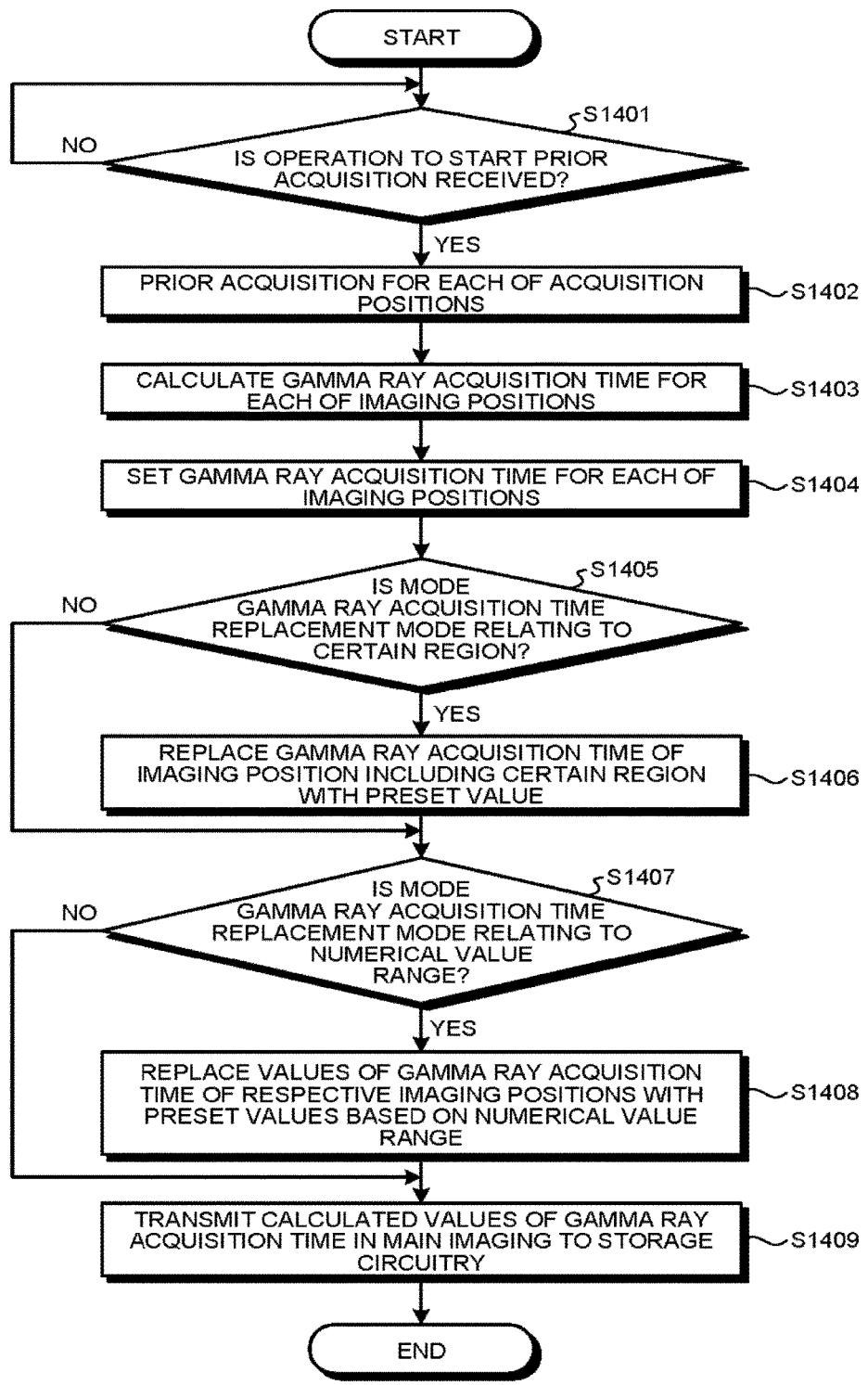

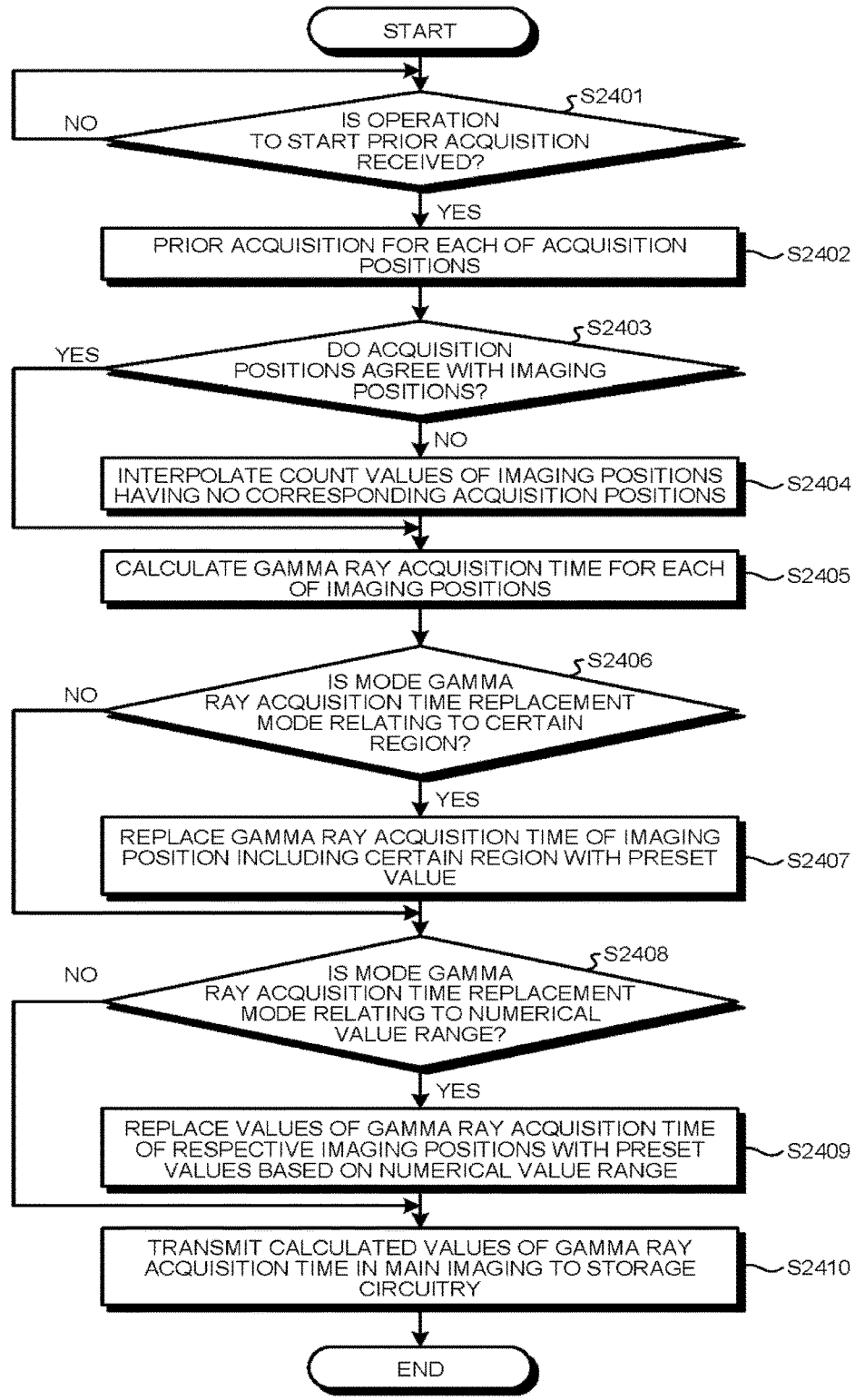

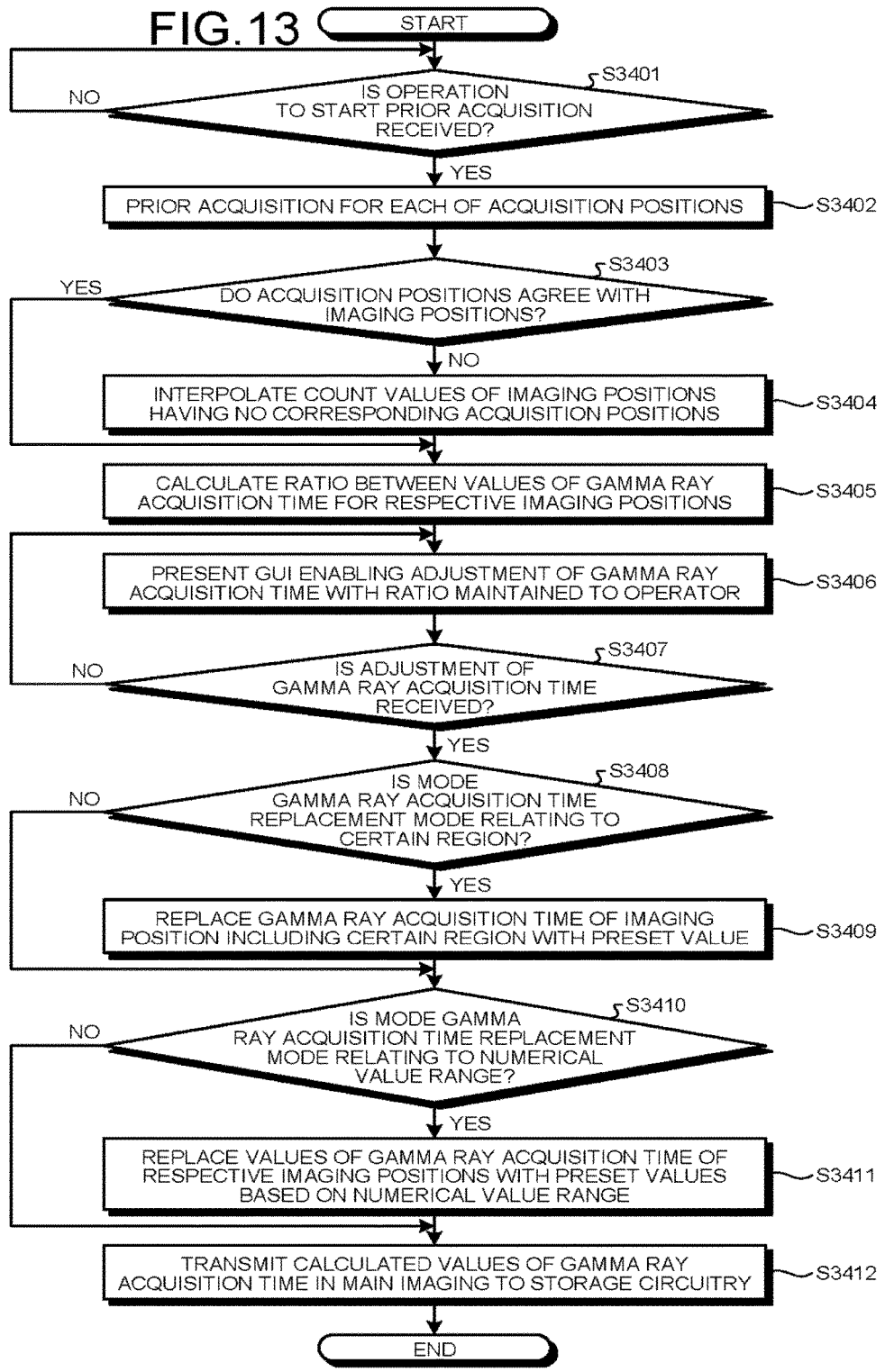

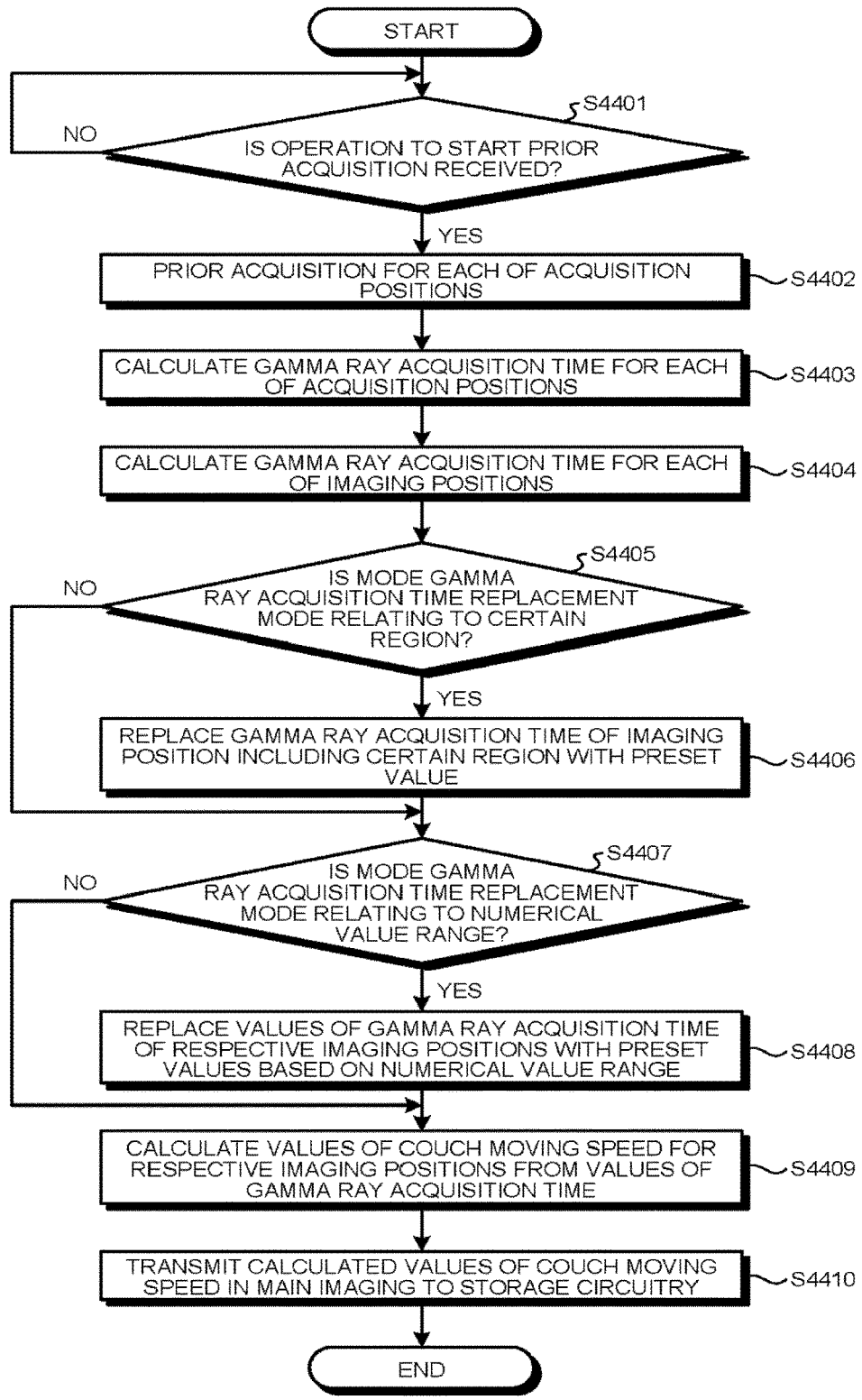

NUCLEAR MEDICINE DIAGNOSTIC APPARATUS AND CONTROL METHOD THEREOF

CROSS-REFERENCE TO RELATED APPLICATIONS

This application is based upon and claims the benefit of priority from Japanese Patent Application No. 2015-159675, filed on Aug. 12, 2015; the entire contents of which are incorporated herein by reference.

FIELD

Embodiments described herein relate generally to a nuclear medicine diagnostic apparatus, and a control method thereof.

BACKGROUND

Positron Emission Computed Tomography (PET) apparatuses are nuclear medicine imaging apparatuses that acquire data relating to pair annihilation events from a subject to which a medicine labeled with positron emission nuclide is administered, to reconstruct a PET image serving as a nuclear medicine image. PET apparatuses reconstruct a PET image indicating tissue distribution of the subject that has taken the medicine, using the phenomenon that two photons (two gamma rays) are emitted in opposite directions when a positron emitted from the medicine is connected with an electron and annihilated.

Generally, the amount of the accumulated medicine differs according to the region of the subject. For this reason, for example, when the time for acquiring gamma rays for each imaging position is fixed in PET imaging, the count values of gamma rays acquired by the PET apparatus become non-uniform between the imaging positions. This non-uniformity may result in non-uniformity in the noise level of the PET image, and deterioration in the inspection efficiency.

BRIEF DESCRIPTION OF THE DRAWINGS

FIG. 1 is a diagram illustrating a whole structure of a PET-CT apparatus according to a first embodiment;
FIG. 5A is a diagram illustrating an example of acquisition positions and imaging positions according to the first embodiment;
FIG. 5B is a diagram illustrating an example of acquisition positions and imaging positions according to the first embodiment
FIG. 5C is a diagram illustrating an example of acquisition positions and imaging positions according to the first embodiment;
FIG. 8 is a flowchart for explaining a flow of a process of the PET-CT apparatus according to the first embodiment;
FIG. 9 is a flowchart for explaining a flow of a process of prior acquisition and calculation of the gamma ray acquisition time according to the first embodiment;
FIG. 11 is a flowchart illustrating a flow of a process of prior acquisition and gamma ray acquisition time according to the second embodiment;
FIG. 13 is a flowchart illustrating a flow of a process of prior acquisition and calculation of gamma ray acquisition time according to the third embodiment;
FIG. 15 is a flowchart illustrating a flow of a process of prior acquisition and calculation of gamma ray acquisition time according to the fourth embodiment.

DETAILED DESCRIPTION

According to an embodiment, a nuclear medicine diagnostic apparatus comprises processing circuitry. The processing circuitry is configured to perform control to execute gamma ray acquisition for main imaging for a subject, and prior acquisition to acquire gamma rays in a plurality of acquisition positions in the subject prior to the main imaging. And the processing circuitry is configured to calculate values of gamma ray acquisition time for respective imaging positions in the main imaging, based on count values of gamma rays acquired in the prior acquisition. And the processing circuitry is configured to perform control to execute the main imaging, based on the calculated values of the gamma ray acquisition time for the respective imaging positions.

Nuclear medicine diagnostic apparatuses according to embodiments will be explained hereinafter with reference to the accompanying drawings. In the following explanation, a PET-CT apparatus, in which a PET apparatus and an X-ray CT apparatus are integrated, will be described as an example, as the nuclear medicine diagnostic apparatus.

First, the whole structure of a PET-CT apparatus according to a first embodiment will be explained hereinafter with reference to FIG. 1. FIG. 1 is a diagram illustrating the whole structure of the PET-CT apparatus according to the first embodiment. As illustrated in FIG. 1, the PET-CT apparatus according to the first embodiment includes a PET gantry 1, a CT gantry 2, a couch device 3, and a console 4.

Figure 2A:
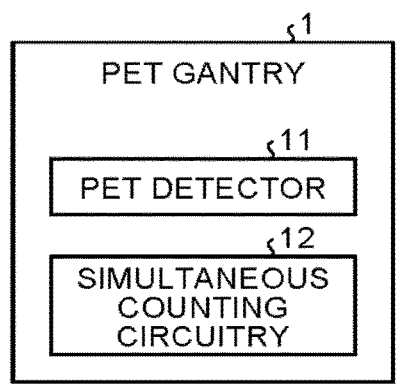
FIG. 2A is a diagram illustrating a structure of a PET gantry according to the first embodiment.
Figure 2B:
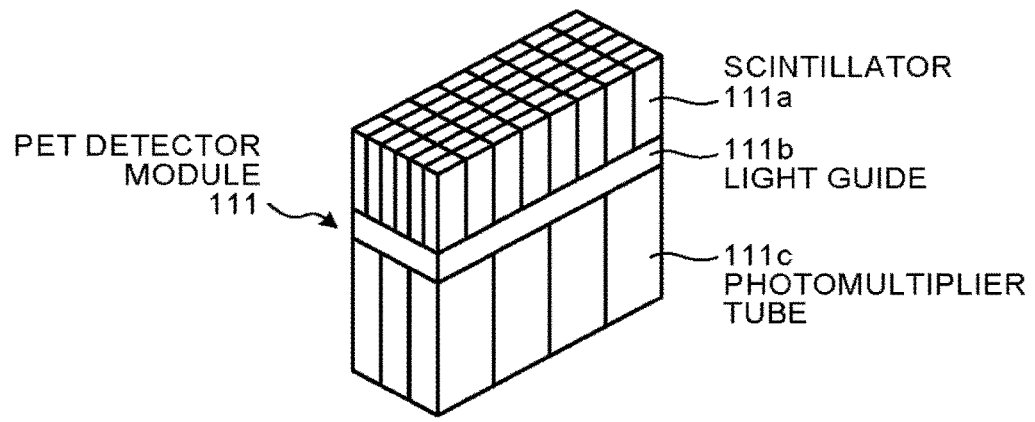
FIG. 2B is a diagram illustrating the structure of the PET gantry according to the first embodiment.

The PET gantry 1 is a device that detects a pair of gamma rays emitted from a living tissue that has taken positron emission nuclide administered to a subject P, to generate projection data (simultaneous counting information) of the gamma rays to reconstruct a PET image. FIG. 2A and FIG. 2B are diagrams illustrating a structure of the PET gantry 1 according to the first embodiment.

As illustrated in FIG. 2A, the PET gantry 1 includes a PET detector 11 and simultaneous counting circuitry 12, and the like. The PET detector 11 is a photon-counting detector that detects gamma rays emitted from the subject P. Specifically, the PET detector 11 is configured by arranging a plurality of PET detector modules 111 in a ring shape to surround the subject P.

For example, each of the PET detector modules 111 is an Anger-type detector including scintillators 111a, photomultiplier tubes (PMT) 111c, and a light guide 111b, as illustrated in FIG. 2B.

The scintillators 111a are a plurality of NaI or EGO arranged in a two-dimensional manner as illustrated in FIG. 2B. NaI and BGO convert the incident gamma rays emitted from the subject P into visible light. The photomultiplier tubes 111c are devices that multiply the visible light output from the scintillators 111a and convert the visible light into an electrical signal. The photomultiplier tubes 111c are arranged densely via the light guide 111b, as illustrated in FIG. 2B. The light guide 111b is used to transmit the visible light output from the scintillators 111a to the photomultiplier tubes 111c, and formed of a plastic material or the like with excellent light transmittance.

Each of the photomultiplier tubes 111c is formed of a photoelectric cathode that receives scintillation light and generates a photoelectron, multi-stage dynodes that supply an electric field to accelerate the generated photoelectron, and an anode serving as a port from which the electron flows. An electron emitted from the photoelectric cathode by photoelectric effect is accelerated toward a dynode, and collides with the surface of the dynode, to output a plurality of electrons. This phenomenon is repeated over multiple stages of dynodes, to multiply the number of electrons in an avalanche manner. At the anode, the number of electrons reaches approximately one million. In such an example, the gain of the photomultiplier tubes 111c is one million times. In addition, to perform amplification using an avalanche phenomenon, a voltage of 1000 volts or more is generally applied between the dynodes and the anode.

As described above, each of the PET detector modules 111 converts gamma rays into visible light with the scintillators 111a, and converts the converted visible light into an electrical signal with the photomultiplier tubes 111c, to count the number of gamma rays emitted from the subject P.

The simultaneous counting circuitry 12 illustrated in FIG. 2A is connected with each of the photomultiplier tubes 111c included in each of the PET detector modules 111. The simultaneous counting circuitry 12 generates simultaneous counting information to determine an incident direction of a pair of gamma rays emitted from positron, from the output result of the PET detector modules 111. Specifically, the simultaneous counting circuitry 12 determines the incident position (positions of the scintillators 111a) of gamma rays, by calculating the gravity center position, based on the positions of the photomultiplier tubes 111c that have converted and outputted the visible light output from the scintillators 111a into electrical signals at the same timing and the intensities of the electrical signals. The simultaneous counting circuitry 12 also calculates the energy values of the incident gamma rays, by calculating (integrating and differentiating) the intensities of the electrical signals output from the respective photomultiplier tubes 111c.

The simultaneous counting circuitry 12 searches (coincidence finding) the output result of the PET detector 11 for a combination in which the incident timings (time) of the gamma rays fall within a time window width of a fixed time and the energy values fall within a fixed energy window width. For example, conditions that are set as search conditions are the time window width of 2 nsec and the energy window width of 350 keV to 550 keV. The simultaneous counting circuitry 12 generates simultaneous counting information (coincidence list), using an output result of the searched combinations as information obtained by simultaneously counting two annihilation photons. Thereafter, the simultaneous counting circuitry 12 transmits the simultaneous counting information to the console 4 illustrated in FIG. 1. A line connecting two detection positions in which two annihilation photons are simultaneously counted is referred to as LOR (Line of Response). The console 4 may generate simultaneous counting information.

The simultaneous counting circuitry 12 may transmit counting information (for example, count values of gamma rays) obtained by counting the gamma rays to the console 4, in addition to transmitting the generated simultaneous counting information to the console 4. The simultaneous counting circuitry 12 may generate and transmit only count values of gamma rays to the console 4, not generating simultaneous counting information.

With reference to FIG. 1 again, the CT gantry 2 according to the present embodiment is a device that detects X-rays transmitted through the subject P, to generate X-ray projection data for generating a diagnostic X-ray CT image. The CT gantry 2 is also capable of generating X-ray projection data to generate two-dimensional or three-dimensional scanogram.

Figure 3:
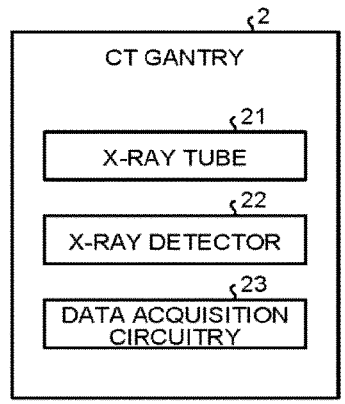
FIG. 3 is a diagram illustrating a structure of a CT gantry according to the first embodiment.

FIG. 3 is a diagram illustrating a structure of the CT gantry 2. As illustrated in FIG. 3, the CT gantry 2 includes an X-ray tube 21, an X-ray detector 22, and data acquisition circuitry 23, and the like. The X-ray tube 21 is a device that generates an X-ray beam, and applies the generated X-ray beam to the subject P. The X-ray detector 22 is a device that detects X-rays transmitted through the subject P, in a position opposed to the X-ray tube 21. Specifically, the X-ray detector 22 is a two-dimensional array detector that detects data (two-dimensional X-ray intensity distribution data) of two-dimensional intensity distribution of X-rays transmitted through the subject P. More specifically, the X-ray detector 22 has a structure in which a plurality of detecting element arrays, in each of which a plurality of channels of X-ray detecting elements are arranged, are arranged along a body axis direction of the subject P. The X-ray tube 21 and the X-ray detector 22 are supported by a rotary frame (not illustrated) inside the CT gantry 2.

The data acquisition circuitry 23 is a data acquisition system (DAS) that performs amplification and A/D conversion on the two-dimensional X-ray intensity distribution data detected by the X-ray detector 22, to generate X-ray projection data. The data acquisition circuitry 23 transmits the X-ray projection data to the console 4 illustrated in FIG. 1.

With reference to FIG. 1 again, the couch device 3 is a bed on which the subject P is placed, and includes a couchtop 31, and a moving base 32. The couch device 3 successively moves the subject to respective imaging ports of the CT gantry 2 and the PET gantry 1, based on an instruction received from the operator of the PET-CT apparatus via the console 4. Specifically, the PET-CT apparatus controls the couch device 3, to perform imaging of an X-ray CT image first, and thereafter perform imaging of a PET image.

The couch device 3 moves the couchtop 31 and the moving base 32 in the body axis direction of the subject, with a driving mechanism (not illustrated). For example, the PET-CT apparatus images an X-ray CT image by helical scan, in which the PET-CT apparatus horizontally moves the couchtop 31 in the direction of the CT gantry 2 while rotating the rotary frame of the CT gantry 2, to helically and successively scan the imaging region of the subject P with X-rays.

After imaging of the X-ray CT image, the PET-CT apparatus horizontally moves the moving base 32 in a state where the couchtop 31 is kept drawn out of the moving base 32, to insert the imaging region of the subject P into the imaging port of the PET gantry 1. In this state, the moving base 32 is moved by the same distance as the distance between the central positions of the respective detectors of the PET gantry 1 and the CT gantry 2, to set the same drawing amount of the couchtop 31 from the moving base 32 when the same region of the subject P in the body axis direction is imaged, between imaging of the X-ray CT image and imaging of the PET image.

Thereafter, the PET-CT apparatus horizontally moves the couchtop 31 in a direction opposite to the moving direction in imaging of the X-ray CT image, to image a PET image. In such a case, the PET-CT apparatus images a wide range of the subject by a step-and-shoot technique in which part of the subject is imaged, thereafter the couchtop 31 is horizontally moved by a predetermined moving amount in a state of stopping imaging, to image another part, and such movement and imaging are repeated. In the following explanation of imaging by the step-and-shoot technique, each of ranges that are imaged in a stepped manner may be referred to as "bed". As another example, the PET-CT apparatus images a wide range of the subject by serial radiography in which the area in which imaging is performed is continuously moved while part of the subject is imaged. In this state, generally the area in which imaging is performed is moved with respect to the subject, by movement of the couch. In the following explanation, in imaging by serial radiography, the speed at which the area in which imaging is performed is moved with respect to the subject may be referred to as "couch moving speed".

The PET-CT apparatus may only draw out the couchtop 31, to move the couchtop 31 to the respective imaging ports of the CT gantry 2 and the PET gantry 1. For example, the PET-CT apparatus may image an X-ray CT image after imaging a PET image.

Figure 4:
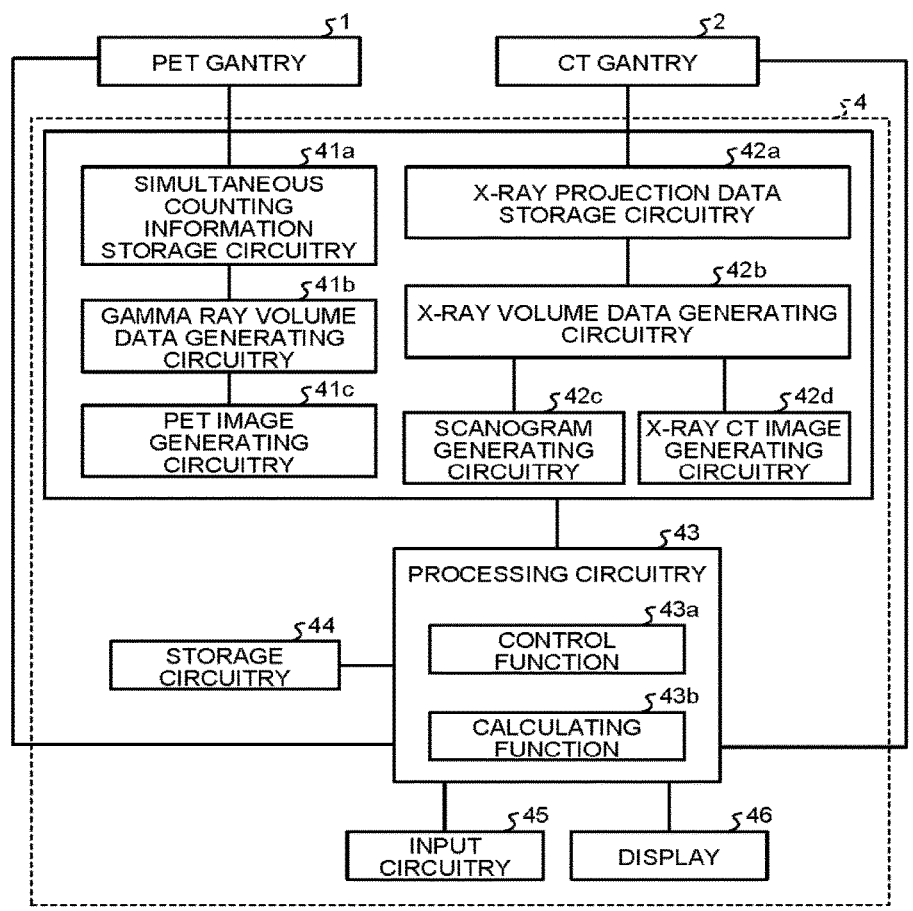
FIG. 4 is a diagram illustrating a structure of a console according to the first embodiment.

The console 4 is a device that receives an instruction from the operator, to control processing performed by the PET-CT apparatus. FIG. 4 is a diagram illustrating a structure of the console 4 according to the first embodiment. As illustrated in FIG. 4, the console 4 includes simultaneous counting information storage circuitry 41*a*, gamma ray volume data generating circuitry 41*b*, PET image generating circuitry 41*c*, X-ray projection data storage circuitry 42*a*, X-ray volume data generating circuitry 42*b*, scanogram generating circuitry 42*c*, X-ray CT image generating circuitry 42*d*, processing circuitry 43, storage circuitry 44, input circuitry 45, and a display 46.

In the embodiment in FIG. 4, the gamma ray volume data generating circuitry 41*b* is a processor that performs reconstruction processing on the simultaneous counting information recorded on the simultaneous counting information storage circuitry 41*a*, to generate gamma ray volume data. The gamma ray volume data generating circuitry 41*b* calls a program corresponding to the reconstruction function from the storage circuitry 44, and executes the program to achieve the reconstruction function. The PET image generating circuitry 41*c* is a processor that performs image generation processing on the gamma ray volume data generated by the gamma ray volume data generating circuitry 41*b*, to generate a PET image. The PET image generating circuitry 41*c* calls a program corresponding to the image generation function from the storage circuitry 44, and executes the program to achieve the image generation function.

In the embodiment illustrated in FIG. 4, the X-ray volume data generating circuitry 42*b* is a processor that performs reconstruction processing on the X-ray projection data recorded on the X-ray projection data storage circuitry 42*a*, to generate X-ray volume data. The X-ray volume data generating circuitry 42*b* calls a program corresponding to the reconstruction function from the storage circuitry 44, and executes the program to achieve the reconstruction function. The scanogram generating circuitry 42*c* is a processor that performs image generation processing on the X-ray volume data generated by the X-ray volume data generating circuitry 42*b*, to generate a scanogram. The X-ray CT image generating circuitry 42*d* is a processor that performs image generation processing on the X-ray volume data generated by the X-ray volume data generating circuitry 42*b*, to generate an X-ray CT image. Each of the scanogram generating circuitry 42*c* and the X-ray CT image generating circuitry 42*d* calls a program corresponding to the image generation function from the storage circuitry 44, and executes the program to achieve the image generation function.

The PET image generating circuitry 41*c*, the scanogram generating circuitry 42*c*, and the X-ray CT image generating circuitry 42*d* are connected to the processing circuitry 43, and output the respective images generated by the image generation function to the processing circuitry 43.

The processing circuitry 43 executes a control function 43*a* and a calculating function 43*b*. In the embodiment in FIG. 4, the processing functions performed in the control function 43*a* and the calculating function 43*b* of the constituent elements are recorded on the storage circuitry 44 in the form of programs executable by the computer. The processing circuitry 43 is a processor that reads a program from the storage circuitry 44, and executes the program to achieve the function corresponding to the program. In other words, the processing circuitry 43 in a state of reading the programs has the respective functions illustrated in the processing circuitry 43 of FIG. 4. FIG. 4 illustrates an example in which single processing circuitry achieves the processing functions performed by the control function 43*a* and the calculating function 43*b*, but processing circuitry may be formed of a combination of a plurality of independent processors, and the processors execute respective programs to achieve the functions.

The term "processor" used in the explanation described above means, for example, a central processing unit (CPU), a graphics processing unit (GPU), or circuitry such as an application specific integrated circuit (ASIC), and a programmable logic device (such as a simple programmable logic device: SPLD), a complex programmable logic device (CPLD), and a field programmable gate array (FPGA)). The processor reads and executes a program stored in the storage circuitry 44, to achieve the function. A program may be directly incorporated into the circuitry of the processor, instead of storing the program in the storage circuitry 44. In such a case, the processor reads and executes the program incorporated into the circuitry, to achieve the function. Each of the processors in the present embodiment is not limited to the case where each processor is formed of single circuitry, but a plurality of independent circuitry may be combined as a processor, to achieve the function. In addition, the constituent elements in FIG. 4 may be integrated into a processor, to achieve the functions.

The control function 43*a* in the first embodiment is an example of control processing performed by the processing circuitry of the claims. The calculating function 43*b* in the first embodiment is an example of calculating processing performed by the processing circuitry of the claims.

The simultaneous counting information storage circuitry 41*a* stores simultaneous counting information transmitted from the simultaneous counting circuitry 12. The simultaneous counting information storage circuitry 41*a* also stores counting information transmitted from the simultaneous counting circuitry 12. The gamma ray volume data generating circuitry 41*b* reconstructs gamma ray volume data by, for example, filtered back projection (FBP) or iterative approximation, from the simultaneous counting information stored in the simultaneous counting information storage circuitry 41*a*. Examples of the iterative approximation are maximum likelihood expectation maximization (MLEM), and ordered subset MLEM (OSEM) with convergence time markedly shortened by improvement in algorithm of MLEM. The PET image generating circuitry 41*c* performs image generation processing on the gamma ray volume data generated by the gamma ray volume data generating circuitry 41*b*, to generate a PET image.

The X-ray projection data storage circuitry 42*a* stores X-ray projection data transmitted from the data acquisition circuitry 23. Specifically, the X-ray projection data storage circuitry 42*a* stores X-ray projection data for reconstructing a scanogram and an X-ray CT image. The X-ray volume data generating circuitry 42*b* performs reconstruction on the X-ray projection data stored in the X-ray projection data storage circuitry 42*a*, by FBP or iterative approximation or the like, to reconstruct X-ray volume data.

The scanogram generating circuitry 42*c* performs image generation processing on the X-ray volume data generated by the X-ray volume data generating circuitry 42*b*, to generate a scanogram used for positioning the subject P and the like. The X-ray CT image generating circuitry 42*d* performs image generation processing on the X-ray volume data stored in the X-ray volume data generating circuitry 42*b*, based on imaging conditions (such as a slice width) determined by the imaging plan, to generate a diagnostic X-ray CT image obtained by imaging a plurality of cross sections orthogonal to the body axis direction of the subject P.

The processing circuitry 43 controls the whole processing performed by the PET-CT apparatus. The processing performed by the PET-CT apparatus includes, specifically, prior acquisition, main imaging, image reconstruction, image generation, and image display. The processing circuitry 43 calculates the imaging conditions in main imaging, based on count values of the gamma rays acquired in prior acquisition, to execute main imaging. This point will be described in detail later. The processing circuitry 43 also receives an operator's instruction from the input circuitry 45.

The storage circuitry 44 stores data used by the processing circuitry 43 for controlling the whole processing performed by the PET-CT apparatus, PET image data, and X-ray CT image data, and the like. The storage circuitry 44 stores programs executed by the processing circuitry 43 and/or the gamma ray volume data generating circuitry 41*b*.

The input circuitry 45 includes a mouse, a keyboard, a trackball, a switch, a button, and/or a joystick used by the operator for inputting various instructions and various settings, and transmits information of instructions and settings received from the operator to the processing circuitry 43. For example, the input circuitry 45 receives a selecting operation of a gamma ray acquisition time replacement mode relating to a certain region, and a gamma ray acquisition time replacement mode relating to the numerical value range, from the operator. The replacement modes for which the input circuitry 45 receives a selecting operation will be described later.

The display 46 is a monitor referred to by the operator. The display 46 displays image data generated by main imaging to the operator, under the control of the processing circuitry 43, and displays a graphical user interface (GUI) for receiving various instructions and various settings from the operator via the input circuitry 45. The display 46 also displays imaging conditions in main imaging. The imaging conditions displayed on the display 46 will be described later.

Under the whole structure of the PET-CT apparatus according to the first embodiment explained above, the PET-CT apparatus according to the first embodiment counts gamma rays emitted from the subject P prior to imaging of a diagnostic PET image, and sets the gamma ray acquisition time in imaging of a diagnostic PET image based on the count value, to improve the inspection efficiency. The imaging of a diagnostic PET image will be referred to as main imaging. The term "prior acquisition" means gamma ray acquisition executed prior to main imaging to calculate the gamma ray acquisition time for each imaging position in main imaging.

First, a conventional PET-CT apparatus will be explained hereinafter. Generally, a PET-CT apparatus can generate a PET image with lower noise level, as the count value of the acquired gamma rays increases. The count value of gamma rays depends on the amount of medicine accumulated in the subject and the gamma ray acquisition time, and the like. Generally, because the accumulated amount of the medicine varies according to the region of the subject, the count values obtained in unit time for the respective imaging positions are not fixed. For this reason, in a conventional PET-CT apparatus, when the acquisition time of gamma rays for each imaging position is fixed, the generated PET image has noise levels that are different between the respective imaging positions, and the inspection efficiency may deteriorate. When data acquisition is performed with the gamma ray acquisition time set longer to reduce the noise level of the PET image in all the imaging positions, longer time is required until the inspection is finished, and the inspection efficiency may deteriorate. Also, in a single photon emission computed tomography (SPECT) apparatus serving as a nuclear medicine imaging apparatus, the inspection efficiency may deteriorate due to the same cause. For this reason, the PET-CT apparatus according to the first embodiment improves the inspection efficiency, by performing control with the processing circuitry 43 explained in detail hereinafter.

Specifically, first, the control function 43a controls execution of prior acquisition prior to main imaging. The following is explanation of positions (acquisition positions) in which prior acquisition is performed on the subject, and positions (imaging positions) in which main imaging is performed on the subject, with reference to FIG. 5A, FIG. 5B, and FIG. 5C. FIG. 5A, FIG. 5B, and FIG. 5C are diagrams illustrating an example of acquisition positions and imaging positions according to the first embodiment. In FIG. 5A and FIG. 5B, the horizontal axis indicates a z axis, and the vertical axis indicates a y axis. FIG. 5A illustrates acquisition positions of prior acquisition for the subject P, and FIG. 5B illustrates imaging positions of main imaging for the subject P.

Q1 to Q7 in FIG. 5A illustrate the case where acquisition positions of prior acquisition are set for respective ranges in which the range for performing gamma ray acquisition is moved in a stepped manner. FIG. 5A illustrates the case where prior acquisition is performed with the ranges that do not overlap each other. The acquisition positions of prior acquisition for the subject P are set as desired. For example, the acquisition positions may be set by the operator, or may automatically be set. R1 to R14 in FIG. 5B illustrate the case where the imaging positions of main imaging are set for respective ranges in which the range for performing gamma ray acquisition is moved in a stepped manner. The imaging positions R1 to R14 illustrate the case where the ranges overlap each other by 50%. The imaging positions are set in accordance with the imaging protocol, or set by the operator as desired. FIG. 5C illustrates the relation between the z coordinates, the acquisition positions, and the imaging positions. z1 to z7 illustrated in FIG. 5A, FIG. 5B, and FIG. 5C indicate the central coordinates of the ranges in the z direction corresponding to the acquisition positions or the imaging positions. For example, both the acquisition position Q1 in FIG. 5A and the imaging position R1 in FIG. 5B have z1 as the central coordinate, and have the same range. By contrast, the range of the imaging range R2 in FIG. 5B overlaps each of the range of the acquisition position Q1 and the range of the acquisition position Q2 in FIG. 5A by 50%, and has a central coordinate in the z axis direction located in a middle position between z1 and z2.

Figure 6A:
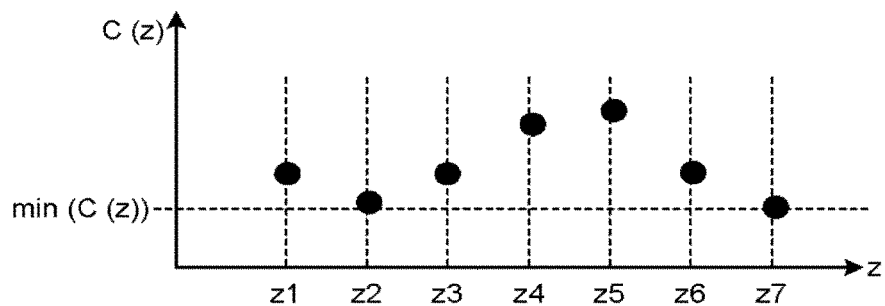
FIG. 6A is a diagram illustrating an example of calculation of gamma ray acquisition time according to the first embodiment.
Figure 6B:
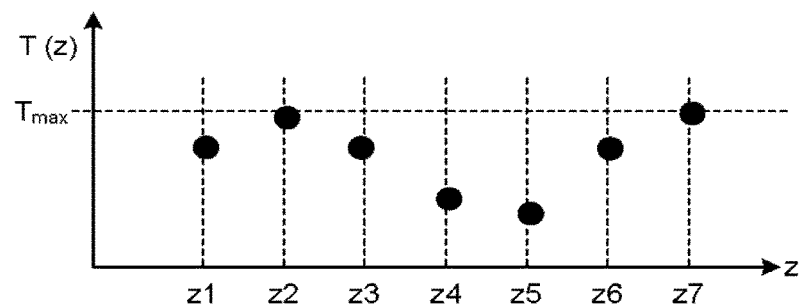
FIG. 6B is a diagram illustrating an example of calculation of the gamma ray acquisition time according to the first embodiment.
Figure 6C:
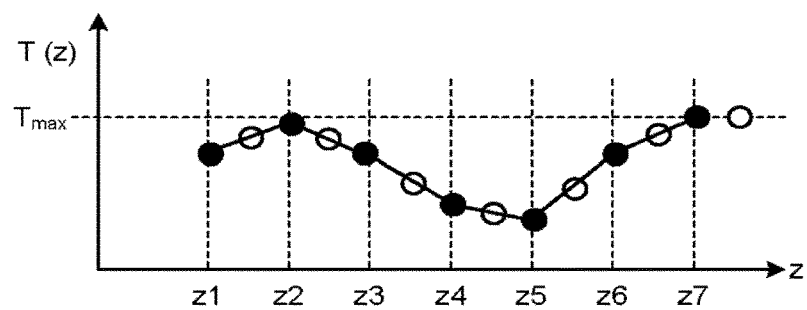
FIG. 6C is a diagram illustrating an example of calculation of the gamma ray acquisition time according to the first embodiment.
Figure 6D:
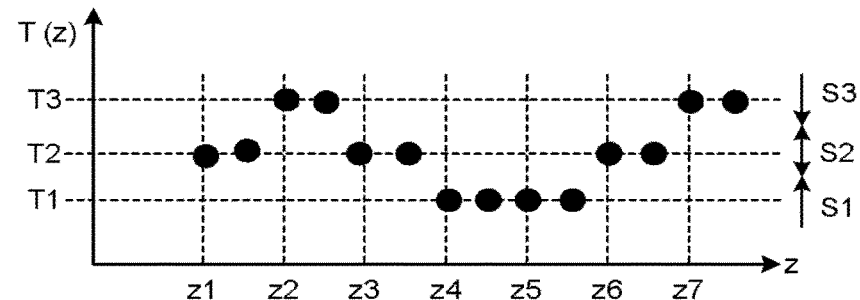
FIG. 6D is a diagram illustrating an example of calculation of the gamma ray acquisition time according to the first embodiment.

The PET-CT apparatus according to the present embodiment acquires gamma rays in advance in the acquisition positions that are set as illustrated in FIG. 5A, and sets values of the gamma ray acquisition time for the respective imaging positions that are set as illustrated in FIG. 5B, based on a result of acquisition. The following is explanation of calculation of values of the gamma ray acquisition time for the respective imaging positions in main imaging, based on the count values of gamma rays acquired for the respective acquisition positions in prior acquisition, with reference to FIG. 6A, FIG. 6B, FIG. 6C, and FIG. 6D. FIG. 6A, FIG. 6B, FIG. 6C, and FIG. 6D are diagrams illustrating an example of calculation of the gamma ray acquisition time. FIG. 6A schematically illustrates a result of prior acquisition, and FIG. 6B, FIG. 6C, and FIG. 6D schematically illustrate calculation of the gamma ray acquisition time based on the result of prior acquisition. "C (z)" in FIG. 6A indicates count values of gamma rays acquired in prior acquisition, and "T (z)" in FIG. 6B, FIG. 6C, and FIG. 6D indicates the gamma ray acquisition time in main imaging.

First, the control function 43a controls the PET gantry 1, to perform prior acquisition in each of the acquisition positions, and count gamma rays as illustrated in FIG. 6A. For example, as illustrated in FIG. 6A, the control function 43a acquires gamma rays for "10 seconds" in each of the acquisition positions corresponding to the central coordinates of z1 to z7. "min (C (z))" illustrated in FIG. 6A is a minimum value of the count value of gamma rays. The acquisition time of gamma rays in prior acquisition can be set to any desired value.

Thereafter, the calculating function 43b calculates the gamma ray acquisition time in main imaging in each of the acquisition positions, as illustrated in FIG. 6B. For example, the calculating function 43b calculates the gamma ray acquisition time in main imaging such that the product of the count value "C (z)" acquired in prior acquisition and the gamma ray acquisition time "T (z)" in main imaging is fixed. For example, the calculating function 43b calculates the gamma ray acquisition time by the following Expression (1).

$$T(z) = T_{max} * \frac{\min(C(z))}{C(z)} \quad (1)$$

"$T_{max}$" in Expression (1) is the maximum acquisition time set for the acquisition position having a count value that is the minimum value in prior acquisition. The maximum acquisition time "$T_{max}$" is set in advance in accordance with the count value. For example, the maximum acquisition time "$T_{max}$" is a constant that is in inverse proportion to the count value, and stored in the storage circuitry 44. For example, the calculating function 43b sets the gamma ray acquisition time in z7 to "$T_{max}$", as illustrated in FIG. 6B, because the count value in z7 in FIG. 6A has the minimum value. The calculating function 43b calculates the gamma ray acquisition time for each of the acquisition positions corresponding to z1 to z6, based on Expression (1) described above, "min (C (z))", and "$T_{max}$".

Thereafter, as illustrated in FIG. 6C, the calculating function 43b calculates values of the gamma ray acquisition time in main imaging for the respective imaging positions. In calculation, the gamma ray acquisition time calculated for the acquisition position having a range agreeing thereto is set for an imaging position having the acquisition position having the same range, as illustrated with black markers in FIG. 6C. By contrast, on imaging positions having no acquisition positions having a range agreeing thereto, the calculating function 43b performs interpolation processing. For example, for an imaging position having no acquisition position having a range agreeing thereto, the calculating function 43b sets an average value of values of the gamma ray acquisition time set for the adjacent imaging positions, as illustrated with white markers in FIG. 6C.

For example, the calculating function 43b may set a smaller value in the values of the gamma ray acquisition time set for the adjacent imaging positions, for an imaging position having no acquisition position having a range agreeing thereto. As an example, when the calculating function 43b sets the gamma ray acquisition time for the imaging position R2 illustrated in FIG. 5B, the calculating function 43b sets the shorter gamma ray acquisition time in the values of the gamma ray acquisition time set for R1 and R3. In addition, the calculating function 43b may set the same gamma ray acquisition time as the gamma ray acquisition time set for the imaging position on the predetermined side in the adjacent imaging positions, for an imaging position having no acquisition position having a range agreeing thereto. As an example, the calculating function 43b sets the gamma ray acquisition time set for the imaging position on the head side of the subject, in the adjacent imaging positions.

As a process of calculation performed by the calculating function 43b to calculate values of the gamma ray acquisition time for the respective imaging positions in main imaging from the count values of gamma rays acquired for the respective acquisition positions in prior acquisition, as described above, the calculating function 43b may calculate values of the gamma ray acquisition time for the respective acquisition positions, and thereafter perform interpolation processing using the gamma ray acquisition time. As another example, the calculating function 43b may calculate the count values of gamma rays of the respective imaging positions by interpolation processing using the count values of gamma rays for the respective acquisition positions, and thereafter calculate values of the gamma ray acquisition time for the respective imaging positions. The calculating function 43b can perform the interpolation processing using the count values of gamma rays for the respective acquisition positions, in the same manner as interpolation processing of values of the gamma ray acquisition time for the respective imaging positions based on the values of gamma ray acquisition time of the respective acquisition positions described above.

As described above, the calculating function 43b calculates values of the gamma ray acquisition time for the respective imaging positions in main imaging, based on the count values of gamma rays counted by prior acquisition. In this manner, the gamma ray acquisition time in main imaging can be set in accordance with gamma rays emitted from each region, to enable acquisition of an image with a properly adjusted image quality in main imaging, and improve the inspection efficiency. For example, as described above, by fixing the product of the count value "C (z)" and the gamma ray acquisition time "T (z)", the noise level in main imaging can be fixed, and the inspection efficiency can be improved.

The PET-CT apparatus according to the first embodiment can replace the calculated gamma ray acquisition time with a preset certain gamma ray acquisition time. For example, the calculating function 43b replaces the values of the gamma ray acquisition time calculated for the respective imaging positions with values of gamma ray acquisition time that are set for the predetermined numerical value ranges. As an example, as illustrated in FIG. 6D, the calculating function 43b replaces the values of the gamma ray acquisition time included in the numerical value range S1 with a preset value T1. In addition, the calculating function 43b replaces the values of the gamma ray acquisition time included in the numerical value range S2 with a preset value T2. The calculating function 43b also replaces the values of the gamma ray acquisition time included in the numerical value range 53 with a preset value T3. The calculating function 43b may set a numerical value range that is equal to or larger than a predetermined upper limit value as a predetermined numerical range, to replace a calculated extremely long gamma ray acquisition time with the numerical range to shorten the acquisition time. The calculating function 43b may set a numerical value range that is equal to or smaller than a predetermined lower limit value as a predetermined numerical range, to replace a calculated extremely short gamma ray acquisition time with the numerical range to extend the acquisition time. As described above, the calculating function 43b replaces the gamma ray acquisition time for each of the predetermined numerical ranges, to avoid setting of gamma ray acquisition time that minutely varies for each of the imaging positions, and setting of an extreme gamma ray acquisition time.

In addition, the calculating function 43b may replace the gamma ray acquisition time in the imaging position including a certain region in the values of the gamma ray acquisition time calculated for the respective imaging positions, with a gamma ray acquisition time that is set in advance according to the certain region. The certain region is a region for which the gamma ray acquisition time can be preset, not based on Expression (1), for a peculiar reason. For example, the certain region is a region such as the bladder that can be expected to have a large count value of gamma rays in prior acquisition because the medicine is easily accumulated therein physiologically. For example, the certain region is a region that does not require detailed imaging in imaging of the whole body of the subject, because the region is to be separately imaged in detail later.

For example, the range of the certain region can be set by extracting the certain region from volume data reconstructed by the X-ray volume data generating circuitry 42b using an analysis application to obtain positional information of regions of the subject. For example, the control function 43a extracts the brain or the bladder by region extraction for the scanogram, and specifies the imaging position including the extracted brain or the bladder. Thereafter, the calculating function 43b replaces the gamma ray acquisition time of the specified imaging position with a preset value. A desired method may be used for extraction of the certain region. For example, the certain region may be extracted based on subject information such as the height, the sitting height, and the gender.

The calculating function 43b may also calculate the gamma ray acquisition time of the imaging position corresponding to the acquisition position including the certain region, based on the count value of gamma rays corresponding to the area excluding the certain region. For example, the calculating function 43b calculates the gamma ray acquisition time in each of the imaging positions such that the product of the count value of gamma rays in the acquisition position not including the certain region and the gamma ray acquisition time in the corresponding imaging position is substantially the same as the product of the count value of gamma rays from the portion other than the certain region in the acquisition position including the certain region and the gamma ray acquisition time in the corresponding imaging position.

The following is explanation of an example of the case where the certain region is the bladder of the subject, and "90%" of gamma rays counted in the acquisition position including the bladder is emitted from the bladder. First, the calculating function 43b obtains the rate "90%" of gamma rays emitted from the bladder among gamma rays counted in the acquisition position including the bladder, from the storage circuitry 44. The rate is stored in, for example, the storage circuitry 44 in advance in association with the imaging conditions, such as the type of the medicine, and the certain region. Thereafter, the calculating function 43b calculates the count value of gamma rays of "10%", in the gamma rays counted in the acquisition position including the bladder, excluding the gamma rays of "90%" emitted from the bladder. The calculating function 43b calculates the gamma ray acquisition time in each of the imaging positions such that the product of the count value of the gamma rays of "10%" emitted from an area excluding the bladder and the gamma ray acquisition time in the corresponding imaging position is substantially the same as the product of the count value of gamma rays in the acquisition position not including the bladder and the gamma ray acquisition time in the corresponding imaging position. In such a case, in main imaging, the calculating function 43b can set the noise level of the area other than the bladder in the imaging position including the bladder to be substantially equal to the noise level in the imaging position not including the bladder, and can improve the accuracy of inspection for the area around the bladder.

The PET-CT apparatus according to the first embodiment can execute and switch a mode of replacing the gamma ray acquisition time in the imaging position including the certain region described above with the predetermined gamma ray acquisition time, and a mode of calculating the gamma ray acquisition time in the imaging position including the certain region based on the count value of gamma rays from the area other than the certain region. Switching of such modes can be automatically performed by the PET-CT apparatus, or by the operator, based on the imaging conditions, such as the type of the medicine, and the purpose of the inspection (such as finding of the primary lesion, and finding of a metastasized part), for example. For example, in inspection to find a metastasized part, because estimating the position of a tumor or the like is difficult, the PET-CT apparatus acquires a PET image having a certain image quality also for the area around the bladder. In such a case, the PET-CT apparatus calculates the gamma ray acquisition time in each of the imaging positions, in the mode of calculating the gamma ray acquisition time in the imaging position including the certain region, based on the count value of gamma rays from the area other than the certain region.

Figure 7:
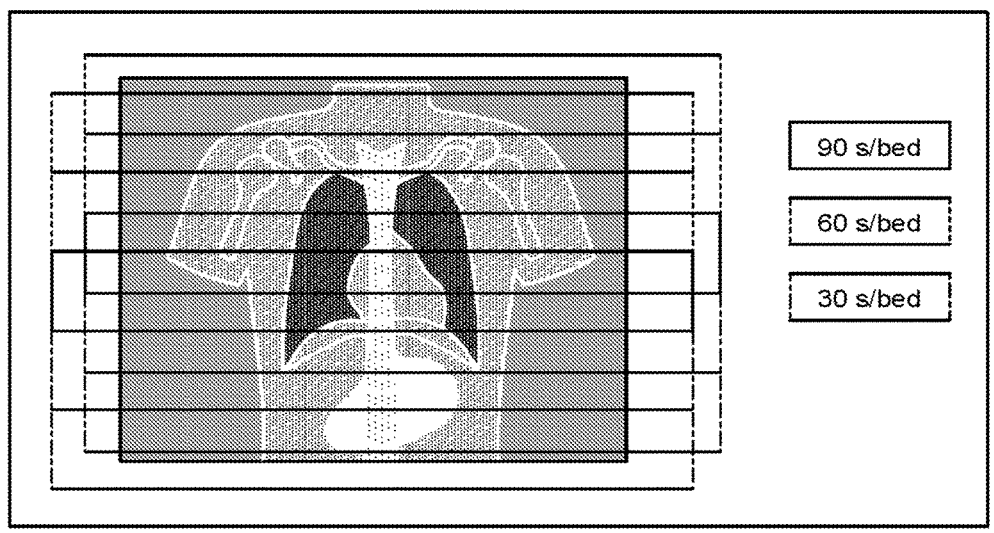
FIG. 7 is a diagram illustrating a display example of a calculation result according to the first embodiment.

As described above, when the gamma ray acquisition time is calculated by the calculating function 43b, the control function 43a performs control to display the calculation result on the display 46. FIG. 7 is a diagram illustrating a display example of the calculation result according to the first embodiment. For example, as illustrated in FIG. 7, the control function 43a displays display information in which information of values of the gamma ray acquisition time calculated for the respective imaging positions are superimposed on the scanogram on the display 46, to present the information to the operator. The control function 43a displays, for example, display information that illustrates the respective imaging positions on the scanogram and enables distinction between values of the gamma ray acquisition time "90 s", "60 s", and "30 s" for the set imaging positions (bed), on the display 46, as illustrated in FIG. 7. As means for distinguishing the values of the gamma ray acquisition time from each other, for example, as illustrated in FIG. 7, the side lines of rectangles indicating the respective imaging positions may be displayed to correspond to the respective values of the gamma ray acquisition time. As another example, colors may be assigned to the respective values of the gamma ray acquisition time, and the rectangles indicating the imaging positions may be displayed with the colors assigned to the set values of the gamma ray acquisition time.

When the display information is displayed on the display 46 as described above, the operator refers to the gamma ray acquisition time of each of the imaging positions displayed on the display 46 to determine whether to start main imaging, and thereafter issues an instruction to start main imaging via the input circuitry 45. When the control function 43a receives an instruction to start main imaging from the input circuitry 45, the control function 43a controls execution of main imaging with the gamma ray acquisition time calculated for each of the imaging positions by the calculating function 43b. The calculating function 43b may receive an operation of changing the gamma ray acquisition time calculated for each of the imaging positions from the operator, in the display.

The following is explanation of an example of a process performed by the PET-CT apparatus with reference to FIG. 8. FIG. 8 is a flowchart for explaining a flow of process performed by the PET-CT apparatus according to the first embodiment. Step S1200, Step S1300, Step S1400, Step S1500, and Step S1600 are steps corresponding to the control function 43a. The steps are steps performed by the processing circuitry 43 calling and executing a predetermined program corresponding to the control function 43a from the storage circuitry 44, to achieve the control function 43a.

After the subject P is set on the couchtop 31 (Step S1100), the processing circuitry 43 determines whether an inspection starting operation is received from the operator (Step S1200). If no inspection starting operation is received in this step (No at Step S1200), the processing circuitry 43 changes to a standby state. By contrast, if an inspection starting operation is received (Yes at Step S1200), the processing circuitry 43 moves the couchtop 31 to the imaging port of the CT gantry 2, and executes imaging of a scanogram on the subject P using X-rays of lower dose than that in imaging of a diagnostic X-ray CT image (Step S1300). Thereafter, the processing circuitry 43 moves the couchtop 31 to the imaging port of the PET gantry 1, executes prior acquisition on the subject P for a shorter time than that of main imaging, and calculates the gamma ray acquisition time in main imaging based on the result of the prior acquisition (Step S1400).

Thereafter, the processing circuitry 43 moves the couchtop 31 to the imaging port of the CT gantry 2, to execute imaging of a diagnostic X-ray CT image on the subject P (Step S1500). Thereafter, the processing circuitry 43 moves the couchtop 31 to the imaging port of the PET gantry 1, executes main imaging on the subject based on the gamma ray acquisition time calculated at Step S1400 (Step S1600). Thereafter, the subject P is brought down from the couch (Step S1700), and the processing is ended.

The flow of the process performed by the PET-CT apparatus according to the first embodiment described above is not limited to the order illustrated in FIG. 8, but the inspection time can be shortened by performing the process in the order illustrated in FIG. 8. As described above, the couchtop 31 on which the subject P lies down and the moving base 32 perform movement of the subject P to the imaging ports of the CT gantry 2 and the PET gantry 1. The moving speed of the moving base 32 is generally slower than the drawing speed of the couchtop 31. Accordingly, the time for movement can be shortened and the inspection time can be reduced, by reducing the number of times of movement of the subject P caused by moving the moving base 32. In the flow of the process illustrated in FIG. 8, prior acquisition is performed after a scanogram is imaged, and thereafter an X-ray CT image is imaged, and a PET image is imaged. When the process is performed in this order, for example, the subject P is moved to the imaging ports of the CT gantry 2 and the PET gantry 1 only by drawing the couchtop 31, and imaging of a scanogram and prior acquisition are performed. Thereafter, after the couchtop 31 is returned to the original position, an X-ray CT image and a PET image are imaged by the process described above. This structure only requires one time of movement of the moving base 32 toward the PET gantry 1, and reduces the time for movement. Imaging of a PET image is desired to be finished in a time as short as possible, for example, within 20 minutes (within 30 minutes including reconstruction). Accordingly, performing the process in the order described above enables the apparatus to deal with such constraint on the inspection time. In the case of the PET-CT apparatus including no moving base 32 and moving the subject P to the imaging ports of the respective devices only by drawing the couchtop 31, the PET-CT apparatus can perform the process in a desired order, as well as the order illustrated in FIG. 8.

Imaging of a scanogram at Step S1300 may not be performed. Imaging of a scanogram and an X-ray CT image at Step S1300 and Step S1500 is performed by helical scan in which the imaging region of the subject P is scanned in a helical manner with X-rays. Imaging of a scanogram at Step S1300 may be performed by scanning the whole body of the subject P along the body axis direction, by moving the couchtop 31 while X-rays are applied from the X-ray tube 21 in a state where the rotary frame is fixed.

The following is explanation of prior acquisition and calculation processing of the gamma ray acquisition time according to the first embodiment with reference to FIG. 9. FIG. 9 is a flowchart for explaining a flow of prior acquisition and a process of calculating the gamma ray acquisition time according to the first embodiment. FIG. 9 illustrates a process corresponding to Step S1400 of FIG. 8.

In FIG. 9, Step S1401 and Step S1402 are steps corresponding to the control function 43a. The steps are steps performed by the processing circuitry 43 calling and executing a predetermined program corresponding to the control function 43a from the storage circuitry 44, to achieve the control function 43a. Step S1403, Step S1404, Step S1405, Step S1406, Step S1407, Step S1408, and Step S1409 are steps corresponding to the calculating function 43b. The steps are steps performed by the processing circuitry 43 calling and executing a predetermined program corresponding to the calculating function 43b from the storage circuitry 44, to achieve the calculating function 43b.

The processing circuitry 43 determines whether an operation to start prior acquisition is received from the operator (Step S1401). If no operation to start prior acquisition is received (No at Step S1401), the processing circuitry 43 changes to a standby state. By contrast, if an operation to start prior acquisition is received (Yes at Step S1401), the processing circuitry 43 controls the PET gantry 1, to perform prior acquisition on the subject P (Step S1402). Thereafter, the processing circuitry 43 calculates the gamma ray acquisition time in main imaging for each of the acquisition positions, based on the count values of gamma rays in prior acquisition (Step S1403). Thereafter, the processing circuitry 43 calculates the gamma ray acquisition time for each of the imaging positions, based on the values of the gamma ray acquisition time calculated for the respective acquisition positions (Step S1404).

The processing circuitry 43 determines whether the operator has selected a gamma ray acquisition time replacement mode relating to the certain region (Step S1405). If the operator has not selected the gamma ray acquisition time replacement mode relating to the certain region (No at Step S1405), the processing circuitry 43 does not perform replacement of the gamma ray acquisition time relating to the certain region. By contrast, if the operator has selected the gamma ray acquisition time replacement mode relating to the certain region (Yes at Step S1405), the processing circuitry 43 replaces the gamma ray acquisition time in the imaging position including the certain region with a preset value (Step S1406).

Thereafter, the processing circuitry 43 determines whether the operator has selected a gamma ray acquisition time replacement mode relating to the numerical value range (Step S1407). If the operator has not selected the gamma ray acquisition time replacement mode relating to the numerical value range (No at Step S1407), the processing circuitry 43 does not perform replacement of the gamma ray acquisition time relating to the numerical value range. By contrast, if the operator has selected the gamma ray acquisition time replacement mode relating to the numerical value range (Yes at Step S1407), the processing circuitry 43 replaces the gamma ray acquisition time in each of the imaging positions with a preset value, based on the predetermined numerical value range (Step S1408). Thereafter, the processing circuitry 43 transmits the calculated gamma ray acquisition time in main imaging to the storage circuitry 44 (Step S1409), and ends the process.

At Step S1403, the processing circuitry 43 can calculate the gamma ray acquisition time for each of the acquisition positions, without using Expression (1). For example, the processing circuitry 43 can calculate the gamma ray acquisition time for each of the acquisition positions such that the product of the count value "C (z)" acquired in prior acquisition and the gamma ray acquisition time "T (z)" in main imaging agrees with the product of the count value acquired in the acquisition position including the reference region in prior acquisition and the reference acquisition time that is preset for the acquisition position including the reference position. The range of the reference region can be extracted by a method similar to that for the certain region described above.

In addition, at Step S1403, for example, the processing circuitry 43 can calculate the gamma ray acquisition time for each of the acquisition positions such that the product of the count value "C (z)" acquired in prior acquisition and the gamma ray acquisition time "T (z)" in main imaging is fixed and the sum of the values of the gamma ray acquisition time for the respective imaging positions amounts to the preset total acquisition time.

As described above, according to the first embodiment, the control function 43a performs control to execute gamma ray acquisition for main imaging for the subject P, and prior acquisition of acquiring gamma rays in a plurality of acquisition positions in the subject P prior to main imaging. The calculating function 43b calculates the values of the gamma ray acquisition time for the respective imaging positions in main imaging, based on the count values of gamma rays in the acquisition positions that are acquired in prior acquisition. The control function 43a performs control to execute the main imaging, based on the calculated values of the gamma ray acquisition time for the respective imaging positions. Accordingly, the PET-CT apparatus according to the first embodiment is capable of setting the gamma ray acquisition time in main imaging in accordance with gamma rays emitted from each region, acquiring an image with a properly adjusted image quality in main imaging, and improving the inspection efficiency.

In addition, according to the first embodiment, the calculating function 43b calculates the values of the gamma ray acquisition time for the respective imaging positions such that the count values of gamma rays for the respective imaging positions in main imaging are substantially fixed, based on the count values of gamma rays in acquisition positions acquired in prior acquisition. Accordingly, the PET-CT apparatus according to the first embodiment enables fixation of the noise level in main imaging, thereby improving the inspection efficiency.

Besides, according to the first embodiment, the calculating function 43b calculates the values of the gamma ray acquisition time for the respective imaging positions such that the product of the count value of gamma rays in each of the acquisition positions acquired in prior acquisition and the value of the gamma ray acquisition time in the imaging position corresponding to the acquisition position is substantially fixed. Accordingly, the PET-CT apparatus according to the first embodiment can easily fix the noise level in main imaging.

According to the first embodiment, the calculating function 43b calculates the values of the gamma ray acquisition time for the respective imaging position such that the gamma ray acquisition time in the imaging position corresponding to the acquisition position having a minimum value of the count value of gamma rays acquired in prior acquisition is equal to or less than a predetermined maximum acquisition time. Accordingly, the PET-CT apparatus according to the first embodiment sets the noise level of the imaging position corresponding to the acquisition position exhibiting the minimum count value to a desired noise level, and can fix the noise level in the other imaging positions.

According to the first embodiment, the calculating function 43b calculates the values of the gamma ray acquisition time for the respective imaging positions such that the sum of values of the gamma ray acquisition time for the respective imaging positions is equal to or less than the predetermined total acquisition time. Accordingly, the PET-CT apparatus according to the first embodiment enables adjustment of the maximum time relating to imaging of a PET image.

According to the first embodiment, the calculating function 43b replaces the gamma ray acquisition time in the imaging position including the certain region among the values of the gamma ray acquisition time calculated for the respective imaging positions, with the gamma ray acquisition time that is preset in accordance with the certain region. Accordingly, the PET-CT apparatus according to the first embodiment enables setting of the optimum gamma ray acquisition time for each region.

According to the first embodiment, the calculating function 43b replaces the gamma ray acquisition time included in the predetermined numerical value range among the values of the gamma ray acquisition time calculated for the respective imaging positions, with the gamma ray acquisition time that is preset according to the numerical value range. The calculating function 43b also sets at least one of a numerical value range that is equal to or larger than the predetermined upper limit value and a numerical value range that is equal to or smaller than the predetermined lower limit value, as the predetermined numerical value range. Accordingly, the PET-CT apparatus according to the first embodiment can avoid the processing load due to minute change in the gamma ray acquisition time between the regions.

According to the first embodiment, the control function 43a displays the calculation result obtained by the calculating function 43b on the display 46. Accordingly, the PET-CT apparatus according to the first embodiment can present the result of the calculated gamma ray acquisition time to the operator.

The first embodiment explained above illustrates the case where the acquisition positions of prior acquisition are set for the whole target area of main imaging. By contrast, a second embodiment illustrates the case where the acquisition positions of prior acquisition are intermittently set for the target area of main imaging. The PET-CT apparatus according to the second embodiment has a structure similar to that of the PET-CT apparatus according to the first embodiment illustrated in FIG. 1, and partly different from that of the first embodiment in the processing in the control function 43a and the calculating function 43b. For this reason, the elements having the same functions as those of the structure explained in the first embodiment will be denoted by the same respective reference numerals as those of FIG. 1, and explanation thereof is omitted.

Figure 10A:
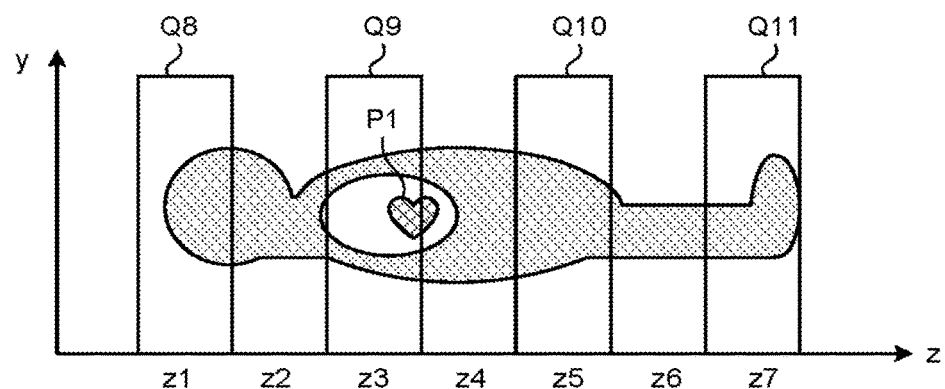
FIG. 10A is a diagram illustrating acquisition positions and calculation of gamma ray acquisition time according to a second embodiment.
Figure 10B:
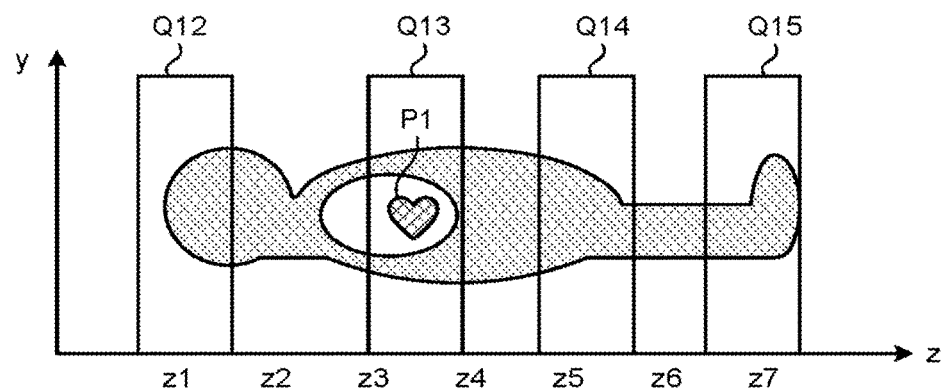
FIG. 10B is a diagram illustrating acquisition positions and calculation of gamma ray acquisition time according to the second embodiment.
Figure 10C:
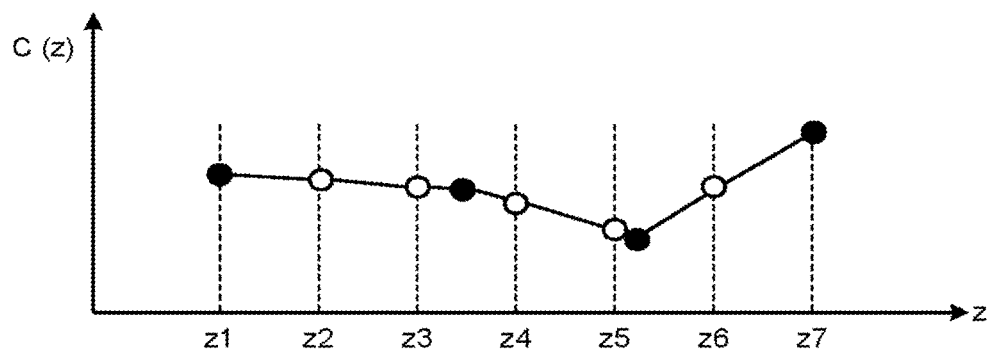
FIG. 10C is a diagram illustrating acquisition positions and calculation of gamma ray acquisition time according to the second embodiment.

The control function 43a according to the second embodiment controls execution of prior acquisition in which gamma rays are counted in acquisition positions that are intermittently set for the area serving as the target of main imaging. The following is explanation of acquisition positions and calculation of the gamma ray acquisition time according to the second embodiment, with reference to FIG. 10A, FIG. 10B, and FIG. 10C. FIG. 10A and FIG. 10B illustrate acquisition positions of prior acquisition for the subject P, and FIG. 10C illustrates a calculation example of count values for respective imaging positions when prior acquisition is performed in the acquisition positions illustrated in FIG. 10B.

The control function 43a according to the second embodiment executes prior acquisition in acquisition positions that are set to desired positions. For example, when the area serving as the target of main imaging is the whole body of the subject P, the control function 43a executes prior acquisition in acquisition positions Q8 to Q11 that are set at regular intervals, as illustrated in FIG. 10A.

In addition, for example, when the area serving as the target of main imaging is the whole body of the subject P, the control function 43a executes prior acquisition in acquisition positions Q12 to Q15 that are intermittently set to include a noted region Pb, as illustrated in FIG. 10B. The noted region P1 is, for example, a region serving as the target of inspection. The range of the noted region P1 can be extracted by a method similar to that for extracting the certain region described above. For example, the control function 43a extracts the noted region P1 by performing region extraction processing on the scanogram. Thereafter, the control function 43a specifies an acquisition position including the noted region P1. For example, the control function 43a sets the couch position (the position of the couchtop 31 moved by the couch device 3) such that prior acquisition is performed in the acquisition position including the noted region P1. The control function 43a may extract in advance the ranges of regions that do not require prior acquisition, and execute prior acquisition in acquisition positions that are intermittently set to avoid the regions that do not require prior acquisition. The regions that do not require prior acquisition are, for example, regions of low interest in inspection, or regions for which the degree of accumulation of the medicine can be expected without prior acquisition.

The PET-CT apparatus according to the present embodiment acquires gamma rays in, for example, acquisition positions that are set as illustrated in FIG. 10B, and sets values of the gamma ray acquisition time for the respective imaging positions in main imaging, based on the result of acquisition. The following is explanation of calculation of values of the gamma ray acquisition time for the respective imaging positions in main imaging, based on the count values of gamma rays acquired for the respective acquisition positions in prior acquisition, with reference to FIG. 10C.

When prior acquisition is performed in the acquisition positions in FIG. 10B, gamma rays are counted in each of the acquisition positions indicated with black markers in FIG. 10C. For example, when main imaging is performed in seven imaging positions having central coordinates of $z1$ to $z7$, the count values of gamma rays in acquisition positions having ranges agreeing with the imaging positions are set for the imaging positions having the central coordinates of $z1$ and $z7$, as illustrated in FIG. 10C. By contrast, the imaging positions having central coordinates of $z2$ to $z6$ have no acquisition positions having ranges agreeing with the imaging positions, and no gamma rays are counted therein. Accordingly, the calculating function 43b according to the second embodiment interpolates count values for the imaging positions having central coordinates of $z2$ to $z6$. As an example, as illustrated in FIG. 10C, the calculating function 43b according to the second embodiment linearly connects the black markers to make a line graph, and calculates count values in the respective imaging positions having $z2$ to $z6$ as the centers, as illustrated with white markers.

In addition, for example, also when imaging positions are set with overlaps of 50% and count values are calculated in the respective imaging positions as illustrated in FIG. 5B, the calculating function 43b calculates count values corresponding to the respective imaging positions using the line graph illustrated in FIG. 10C. For the imaging position having no acquisition position having a range agreeing with that of the imaging position, the calculating function 43b may set a smaller value in the count values counted in the adjacent acquisition positions. As another example, for the imaging position having no acquisition position having a range agreeing with that of the imaging position, the calculating function 43b may set the same value as the count value counted in the acquisition position on the predetermined side in the adjacent acquisition positions, for example. As another example, for the imaging position having no acquisition position having a range agreeing with that of the imaging position, the calculating function 43b may set the count value in the closest acquisition position, for example.

As described above, when the calculating function 43b calculates the count values of the respective imaging positions, the calculating function 43b calculates values of the gamma ray acquisition time of the respective imaging positions, in the same manner as the first embodiment. Thereafter, the control function 43a displays the calculation result on the display 46.

The following is explanation of prior acquisition and calculation processing of the gamma ray acquisition time according to the second embodiment, with reference to FIG. 11. FIG. 11 is a flowchart for explaining a flow of a process of prior acquisition and calculation of the gamma ray acquisition time according to the second embodiment.

In FIG. 11, Step S2401 and Step S2402 are steps corresponding to the control function 43a. The steps are steps performed by the processing circuitry 43 calling and executing a predetermined program corresponding to the control function 43a from the storage circuitry 44, to achieve the control function 43a. Step S2403, Step S2404, Step S2405, Step S2406, Step S2407, Step S2408, Step S2409, and Step S2410 are steps corresponding to the calculating function 43b. The steps are steps performed by the processing circuitry 43 calling and executing a predetermined program corresponding to the calculating function 43b from the storage circuitry 44, to achieve the calculating function 43b.

The processing circuitry 43 determines whether an operation to start prior acquisition is received from the operator (Step S2401). If no operation to start prior acquisition is received (No at Step S2401), the processing circuitry 43 changes to a standby state. By contrast, if an operation to start prior acquisition is received (Yes at Step S2401), the processing circuitry 43 controls the PET gantry 1, to perform prior acquisition on the subject P (Step S2402). Thereafter, the processing circuitry 43 determines whether the ranges of the acquisition positions and the imaging positions agree with each other (Step S2403). If the ranges of the acquisition positions and the imaging positions agree with each other (Yes at Step S2403), the processing circuitry 43 sets the count values acquired in the acquisition positions having respective ranges agreeing with those of the imaging positions for the respective imaging positions. By contrast, if the ranges of the acquisition positions and the imaging positions do not agree with each other (No at Step S2403), the processing circuitry 43 sets the count value acquired in the acquisition position having a range agreeing with the imaging position for the imaging position having the acquisition position having a range agreeing with the range of the imaging position, and interpolates the count value for the imaging position having no acquisition position having a range agreeing with the range of the imaging position (Step S2404). Thereafter, the processing circuitry 43 calculates values of the gamma ray acquisition time for the respective imaging positions, based on the count values set for the respective imaging positions (Step S2405).

Thereafter, the processing circuitry 43 determines whether the operator has selected the gamma ray acquisition time replacement mode relating to the certain region (Step S2406). If the operator has not selected the gamma ray acquisition time replacement mode relating to the certain region (No at Step S2406), the processing circuitry 43 does not perform replacement of the gamma ray acquisition time relating to the certain region. By contrast, if the operator has selected the gamma ray acquisition time replacement mode relating to the certain region (Yes at Step S2406), the processing circuitry 43 replaces the gamma ray acquisition time in the imaging position including the certain region with a preset value (Step S2407).

Thereafter, the processing circuitry 43 determines whether the operator has selected the gamma ray acquisition time replacement mode relating to the numerical value range (Step S2408). If the operator has not selected the gamma ray acquisition time replacement mode relating to the numerical value range (No at Step S2408), the processing circuitry 43 does not perform replacement of the gamma ray acquisition time relating to the numerical value range. By contrast, if the operator has selected the gamma ray acquisition time replacement mode relating to the numerical value range (Yes at Step S2408), the processing circuitry 43 replaces the gamma ray acquisition time in each of the imaging positions with a preset value, based on the predetermined numerical value range (Step S2409). Thereafter, the processing circuitry 43 transmits the calculated gamma ray acquisition time in main imaging to the storage circuitry 44 (Step S2410), and ends the process.

As described above, according to the second embodiment, the control function 43a performs control to execute prior acquisition to acquire gamma rays in a plurality of acquisition positions that are intermittently set for the target area of main imaging. Accordingly, the PET-CT apparatus according to the second embodiment can shorten the time required for prior acquisition, and improve the inspection efficiency.

In addition, according to the second embodiment, the control function 43a sets a plurality of acquisition positions such that at least one of the acquisition positions includes the noted region. Accordingly, the PET-CT apparatus according to the second embodiment enables setting of acquisition positions in accordance with the details of the inspection, thereby further improving the inspection efficiency.

The first embodiment illustrates the case in which the PET-CT apparatus automatically calculates values of the gamma ray acquisition time for the respective imaging positions in main imaging. By contrast, a third embodiment illustrates the case where the PET-CT apparatus automatically calculates the ratio between the values of the gamma ray acquisition time for the respective imaging positions in main imaging, and the operator designates specific values of the gamma ray acquisition time. The PET-CT apparatus according to the third embodiment has a structure similar to that of the PET-CT apparatus according to the first embodiment illustrated in FIG. 1, and partly different from that of the first embodiment in the processing in the control function 43a and the calculating function 43b. For this reason, the elements having the same functions as those of the structure explained in the first embodiment will be denoted by the same respective reference numerals as those of FIG. 1, and explanation thereof is omitted.

Figure 12A:
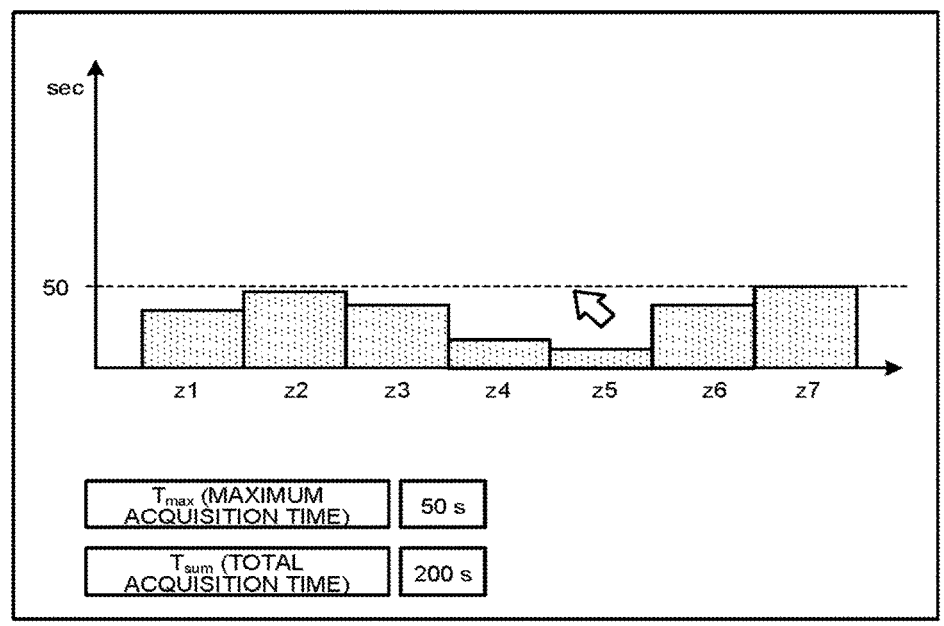
FIG. 12A is a diagram illustrating an example of calculation of gamma ray acquisition time according to a third embodiment.
Figure 12B:
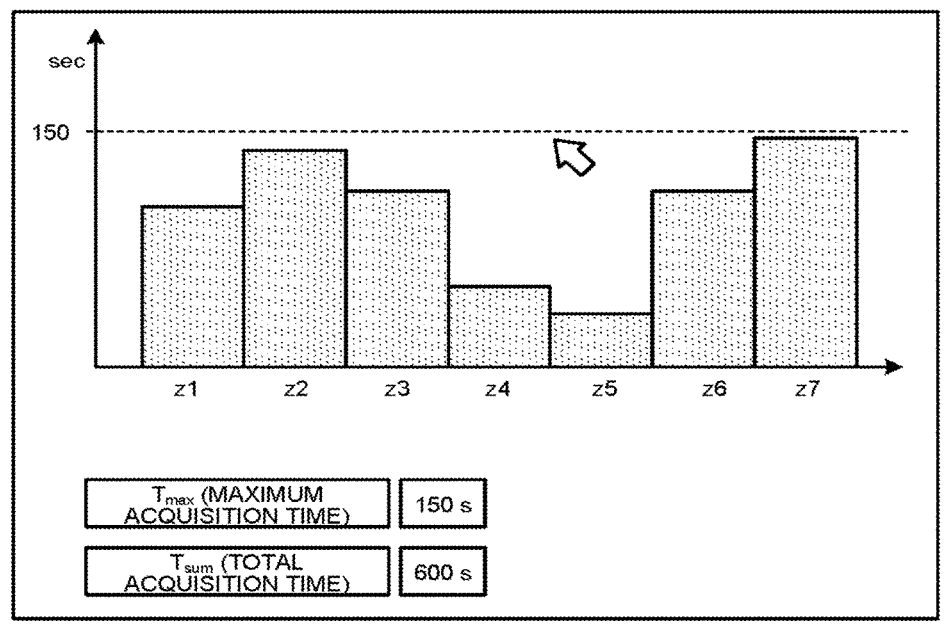
FIG. 12B is a diagram illustrating an example of calculation of gamma ray acquisition time according to the third embodiment.

The calculating function 43b according to the third embodiment calculates the ratio between the values of the gamma ray acquisition time in the respective imaging positions such that the product of the count value "C (z)" acquired in prior acquisition and the gamma ray acquisition time "T (z)" in main imaging is fixed in each of the imaging positions. The control function 43a according to the third embodiment presents, for example, a GUI as illustrated in FIG. 12A to the operator. For the GUI of FIG. 12A, the operator adjusts the values in the gamma ray acquisition time in the respective imaging positions, as illustrated in FIG. 12B, via the input circuitry 45, while maintaining the ratio between the values of the gamma ray acquisition time in the respective imaging positions. The operator settles the specific values of the gamma ray acquisition time in main imaging, with reference to the maximum acquisition time $T_{max}$ serving as the gamma ray acquisition time for the imaging position with the longest gamma ray acquisition time, and the total acquisition time $T_{sum}$ serving as the sum of the values of the gamma ray acquisition time in the respective imaging positions.

In this processing, an upper limit value may be preset for the maximum acquisition time $T_{max}$, and the operator may adjust the values of the gamma ray acquisition time in main imaging within the range in which $T_{max}$ is equal to or smaller than the upper limit value. In addition, an upper limit value may be preset for the total acquisition time $T_{sum}$, and the operator may adjust the values of the gamma ray acquisition time in main imaging within the range in which $T_{sum}$ is equal to or smaller than the upper limit value. An upper limit value may be preset for the gamma ray acquisition time in the imaging position including the reference region, and the operator may adjust the values of the gamma ray acquisition time in main imaging within the range in which the gamma ray acquisition time in the imaging position including the reference region is equal to or smaller than the upper limit value. FIG. 12A and FIG. 12B are diagrams illustrating an example of calculation of values of the gamma ray acquisition time according to the third embodiment.

The following is explanation of prior acquisition and processing of calculating the gamma ray acquisition time according to the third embodiment, with reference to FIG. 13. FIG. 13 is a flowchart for explaining a flow of a process of prior acquisition and the process of calculating the gamma ray acquisition time according to the third embodiment.

In FIG. 13, Step S3401, Step S3402, Step S3406, and Step S3407 are steps corresponding to the control function 43a. The steps are steps performed by the processing circuitry 43 calling and executing a predetermined program corresponding to the control function 43a from the storage circuitry 44, to achieve the control function 43a. Step S3403, Step S3404, Step S3405, Step S3408, Step S3409, Step S3410, Step S3411, and Step S3412 are steps corresponding to the calculating function 43b. The steps are steps performed by the processing circuitry 43 calling and executing a predetermined program corresponding to the calculating function 43b from the storage circuitry 44, to achieve the calculating function 43b.

The processing circuitry 43 determines whether an operation to start prior acquisition is received from the operator (Step S3401). If no operation to start prior acquisition is received (No at Step S3401), the processing circuitry 43 changes to a standby state. By contrast, if an operation to start prior acquisition is received (Yes at Step S3401), the processing circuitry 43 controls the PET gantry 1, to perform prior acquisition on the subject P (Step S3402). Thereafter, the processing circuitry 43 determines whether the ranges of the acquisition positions and the imaging positions agree with each other (Step S3403). If the ranges of the acquisition positions and the imaging positions agree with each other, the processing circuitry 43 sets the count values acquired in the acquisition positions having respective ranges agreeing with those of the imaging positions for the respective imaging positions (Yes at Step S3403). By contrast, if the ranges of the acquisition positions and the imaging positions do not agree with each other (No at Step S3403), the processing circuitry 43 sets the count value acquired in the acquisition position having a range agreeing with the imaging position for the imaging position having the acquisition position having a range agreeing with the range of the imaging position, and interpolates the count value for the imaging position having no acquisition position having a range agreeing with the range of the imaging position (Step S3404). Thereafter, the processing circuitry 43 calculates the ratio between values of the gamma ray acquisition time for the respective imaging positions, based on the count values set for the respective imaging positions (Step S3405).

Thereafter, the processing circuitry 43 presents a GUI that enables adjustment of the gamma ray acquisition time with the ratio between the values of the gamma ray acquisition time maintained, to the operator (Step S3406). The processing circuitry 43 determines whether adjustment of the gamma ray acquisition time is received (Step S3407). If no adjustment of the gamma ray acquisition time is received (No at Step S3407), the processing circuitry 43 changes to the standby state. By contrast, if adjustment of the gamma ray acquisition time is received (Yes at Step S3407), the processing circuitry 43 determines whether the operator has selected the gamma ray acquisition time replacement mode relating to the certain region (Step S3408). If the operator has not selected the gamma ray acquisition time replacement mode relating to the certain region (No at Step S3408), the processing circuitry 43 does not perform replacement of the gamma ray acquisition time relating to the certain region. By contrast, if the operator has selected the gamma ray acquisition time replacement mode relating to the certain region (Yes at Step S3408), the processing circuitry 43 replaces the gamma ray acquisition time in the imaging position including the certain region with a preset value (Step S3409).

Thereafter, the processing circuitry 43 determines whether the operator has selected the gamma ray acquisition time replacement mode relating to the numerical value range (Step S3410). If the operator has not selected the gamma ray acquisition time replacement mode relating to the numerical value range (No at Step S3410), the processing circuitry 43 does not perform replacement of the gamma ray acquisition time relating to the numerical value range. By contrast, if the operator has selected the gamma ray acquisition time replacement mode relating to the numerical value range (Yes at Step S3410), the processing circuitry 43 replaces the gamma ray acquisition time in each of the imaging positions with a preset value, based on the predetermined numerical value range (Step S3411). Thereafter, the processing circuitry 43 transmits the calculated gamma ray acquisition time in main imaging to the storage circuitry 44 (Step S3412), and ends the process.

As described above, the third embodiment provides the structure of calculating the ratio between the values of the gamma ray acquisition time for the respective imaging positions in main imaging based on a result of prior acquisition, to equalize the noise levels of the respective imaging positions in main imaging, and enables the operator to set specific values of the gamma ray acquisition time in main imaging according to the purpose of inspection. Accordingly, the third embodiment can improve the inspection efficiency.

The first embodiment illustrates the case where prior acquisition and main imaging are performed by the step-and-shoot technique to move the range in which gamma ray acquisition is performed in a stepped manner. By contrast, a fourth embodiment illustrates the case where prior acquisition and main imaging are performed by serial radiography in which the range in which imaging is performed is continuously moved. The PET-CT apparatus according to the fourth embodiment has a structure similar to that of the PET-CT apparatus according to the first embodiment illustrated in FIG. 1, and partly different from that of the first embodiment in the processing in the control function 43*a* and the calculating function 43*b*. For this reason, the elements having the same functions as those of the structure explained in the first embodiment will be denoted by the same respective reference numerals as those of FIG. 1, and explanation thereof is omitted.

Figure 14A:
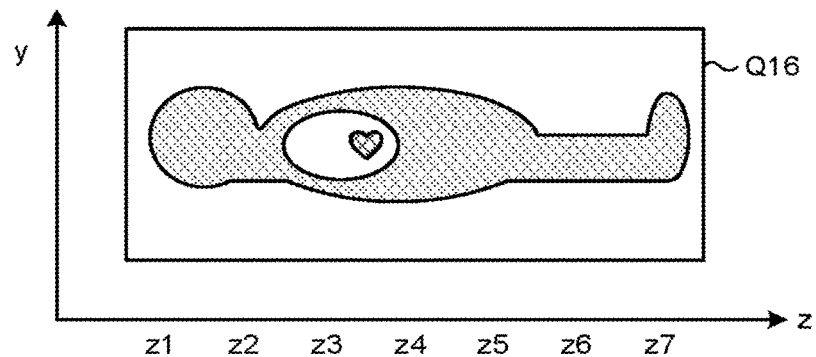
FIG. 14A is a diagram illustrating an example of calculation of gamma ray acquisition time and couch moving speed according to a fourth embodiment.
Figure 14B:
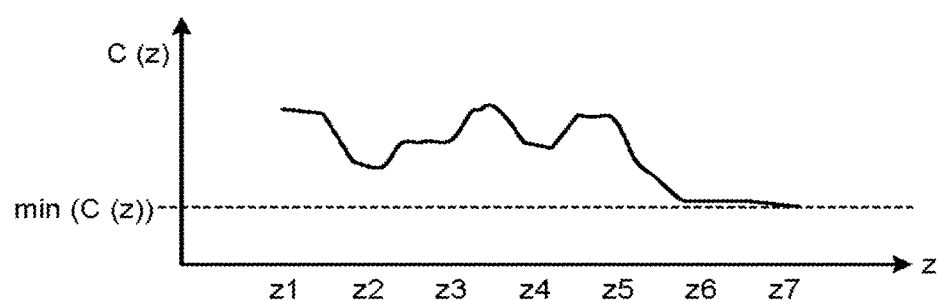
FIG. 14B is a diagram illustrating an example of calculation of gamma ray acquisition time and couch moving speed according to the fourth embodiment.
Figure 14C:
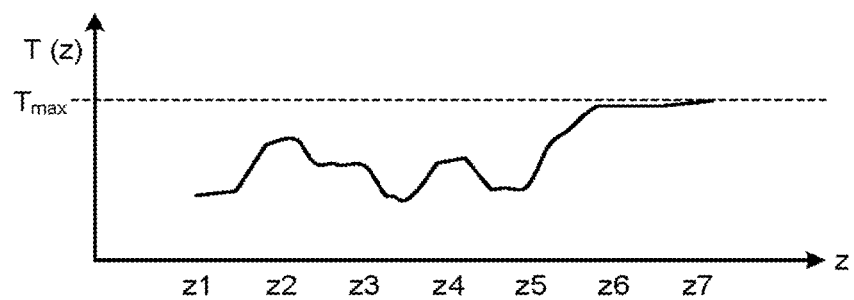
FIG. 14C is a diagram illustrating an example of calculation of gamma ray acquisition time and couch moving speed according to the fourth embodiment.
Figure 14D:
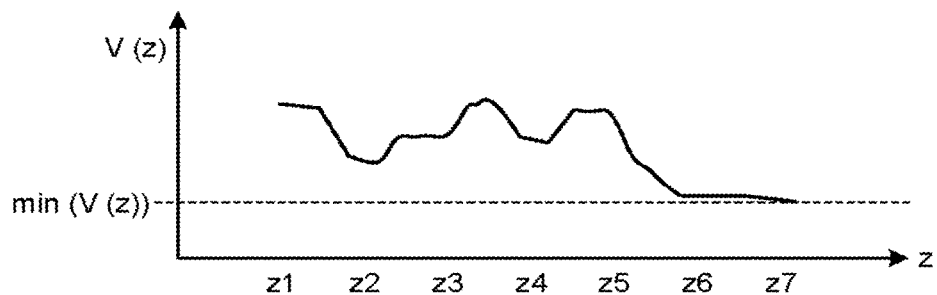
FIG. 14D is a diagram illustrating an example of calculation of gamma ray acquisition time and couch moving speed according to the fourth embodiment.

The control function 43*a* according to the fourth embodiment executes prior acquisition and main imaging by serial radiography. The following is explanation of acquisition positions, imaging positions, and calculation of the gamma ray acquisition time according to the fourth embodiment, with reference to FIG. 14A, FIG. 14B, FIG. 14C, and FIG. 14D. FIG. 14A, FIG. 14B, FIG. 14C, and FIG. 14D are diagrams illustrating an example of calculation of the gamma ray acquisition time and the couch moving speed according to the fourth embodiment. FIG. 14A illustrates the target area of main imaging and prior acquisition. The following description illustrates the case where the whole body of the subject P serves as the target area of main imaging and the target area of prior acquisition, as illustrated with Q16 of FIG. 14A, as an example. FIG. 14B illustrates count values of gamma rays obtained in prior acquisition in the respective acquisition positions. FIG. 14C illustrates values of the gamma ray acquisition time in main imaging calculated for the respective imaging positions. FIG. 14D illustrates values of the couch moving speed in main imaging calculated for the respective imaging positions.

When prior acquisition is performed by serial radiography, the count value of gamma rays continuously changes with respect to the z coordinate, as illustrated in FIG. 14B. The control function 43*a* according to the fourth embodiment regards Q16 illustrated in FIG. 14A as an assembly of innumerable acquisition positions divided in the z axis direction, and regards the count value of gamma rays illustrated in FIG. 14B as count values in the respective innumerable acquisition positions. In this manner, the control function 43*a* is capable of calculating values of the gamma ray acquisition time in the respective imaging positions, as illustrated in FIG. 14C, based on the count values in the respective acquisition positions. The control function 43*a* according to the fourth embodiment also executes main imaging, based on the values of the gamma ray acquisition time calculated for the respective imaging positions.

The calculating function 43*b* according to the fourth embodiment calculates values of the gamma ray acquisition time for the respective imaging positions, as imaging conditions in the case where main imaging is executed by serial radiography. When the apparatus requires setting of the speed (couch moving speed) V (z) at which the position for acquiring gamma rays is moved with respect to the subject P, as the imaging condition, the calculating function 43*b* according to the fourth embodiment is capable of calculating the couch moving speed V (z) in each imaging position, as illustrated in FIG. 14D, by dividing the width in the z axis direction in which gamma rays can be acquired in each instance by the gamma ray acquisition time of the imaging position. Specifically, the gamma ray acquisition time T (z) is in simple inverse proportion to the couch moving speed V (z), and calculating the gamma ray acquisition time for each imaging position is synonymous with calculating the moving speed for each imaging position.

The following is explanation of prior acquisition and processing of calculating the gamma ray acquisition time according to the fourth embodiment, with reference to FIG. 15. FIG. 15 is a flowchart for explaining a flow of a process of prior acquisition and the processing of calculating the gamma ray acquisition time according to the fourth embodiment.

In FIG. 15, Step S4401 and Step S4402 are steps corresponding to the control function 43*a*. The steps are steps performed by the processing circuitry 43 calling and executing a predetermined program corresponding to the control function 43*a* from the storage circuitry 44, to achieve the control function 43*a*. Step S4403, Step S4404, Step S4405, Step S4406, Step S4407, Step S4408, Step S4409, and Step S4410 are steps corresponding to the calculating function 43*b*. The steps are steps performed by the processing circuitry 43 calling and executing a predetermined program corresponding to the calculating function 43*b* from the storage circuitry 44, to achieve the calculating function 43*b*.

The processing circuitry 43 determines whether an operation to start prior acquisition is received from the operator (Step S4401). If no operation to start prior acquisition is received (No at Step S4401), the processing circuitry 43 changes to a standby state. By contrast, if an operation to start prior acquisition is received (Yes at Step S4401), the processing circuitry 43 controls the PET gantry 1, to perform prior acquisition on the subject P (Step S4402). Thereafter, the processing circuitry 43 calculates values of the gamma ray acquisition time in main imaging for the respective acquisition positions, based on the count values of gamma rays in prior acquisition (Step S4403). Thereafter, the processing circuitry 43 calculates values of the gamma ray acquisition time for the respective imaging positions, based on the values of the gamma ray acquisition time calculated for the respective acquisition positions (Step S4404).

The processing circuitry 43 determines whether the operator has selected the gamma ray acquisition time replacement mode relating to the certain region (Step S4405). If the operator has not selected the gamma ray acquisition time replacement mode relating to the certain region (No at Step S4405), the processing circuitry 43 does not perform replacement of the gamma ray acquisition time relating to the certain region. By contrast, if the operator has selected the gamma ray acquisition time replacement mode relating to the certain region (Yes at Step S4405), the processing circuitry 43 replaces the gamma ray acquisition time in the imaging position including the certain region with a preset value (Step S4406).

Thereafter, the processing circuitry 43 determines whether the operator has selected the gamma ray acquisition time replacement mode relating to the numerical value range (Step S4407). If the operator has not selected the gamma ray acquisition time replacement mode relating to the numerical value range (No at Step S4407), the processing circuitry 43 does not perform replacement of the gamma ray acquisition time relating to the numerical value range. By contrast, if the operator has selected the gamma ray acquisition time replacement mode relating to the numerical value range (Yes at Step S4407), the processing circuitry 43 replaces values of the gamma ray acquisition time in the respective imaging positions with preset values, based on the predetermined numerical value ranges (Step S4408). Thereafter, the processing circuitry 43 calculates values of the couch moving speed for the respective imaging positions from the values of the gamma ray acquisition time for the respective imaging positions (Step S4409). Thereafter, the processing circuitry 43 transmits the calculated values of the couch moving speed in main imaging to the storage circuitry 44 (Step S4410), and ends the processing.

At Step S4410, the processing circuitry 43 may transmit the values of the gamma ray acquisition time for the respective imaging positions to the storage circuitry 44, together with, or instead of, the calculated values of the couch moving speed for the respective imaging positions.

The processing circuitry 43 may calculate the couch moving speed by multiplying a predetermined coefficient by the count value of gamma rays, without calculating the gamma ray acquisition time. In addition, the processing circuitry 43 may perform one of prior acquisition and main imaging by serial radiography, and perform the other by the step-and-shoot technique.

As described above, the fourth embodiment provides the structure of calculating values of the gamma ray acquisition time for the respective imaging positions in main imaging from a result of prior acquisition, in the case where main imaging is executed by serial radiography, to enable equalization of the noise levels in the respective imaging positions. Accordingly, the fourth embodiment can improve the inspection efficiency in the case where main imaging is executed by serial radiography.

In addition to the first to the fourth embodiments described above, various different embodiments may be executed.

The first embodiment described above illustrates display information that displays distinguishably the values of the gamma ray acquisition time set for the respective imaging positions (beds), as illustrated in FIG. 7. However, the embodiment is not limited thereto, but display information may be displayed in various forms. The following is explanation of variation of display examples of the display information.

The PET-CT apparatus according to a fifth embodiment has a structure similar to that of the PET-CT apparatus according to the first embodiment illustrated in FIG. 1, and partly different from that of the first embodiment in the processing in the control function 43a. For this reason, the elements having the same functions as those of the structure explained in the first embodiment will be denoted by the same respective reference numerals as those of FIG. 1, and explanation thereof is omitted.

Figure 16A:
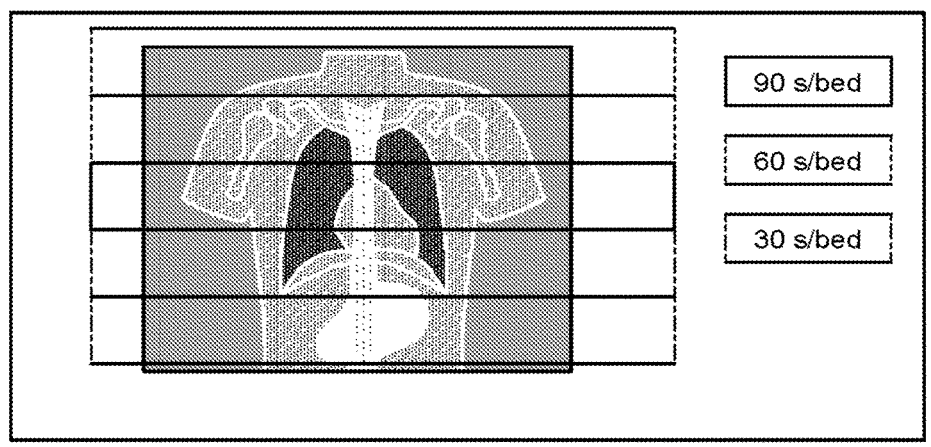
FIG. 16A is a diagram illustrating a display example of a calculation result according to a fifth embodiment.
Figure 16B:
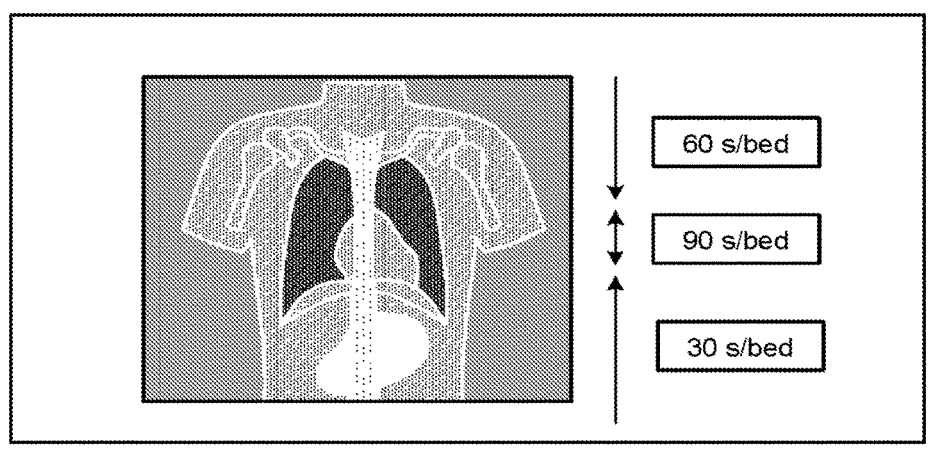
FIG. 16B is a diagram illustrating a display example of a calculation result according to the fifth embodiment.

FIG. 16A and FIG. 16B are diagrams illustrating a display example of a calculation result according to the fifth embodiment. For example, the control function 43a according to the fifth embodiment is capable of displaying a calculation result on the display 46 as illustrated in FIG. 16A, to present the calculation result to the operator. When main imaging is executed by serial radiography and the imaging positions do not overlap each other, for example, the control function 43a displays display information indicating values of the gamma ray acquisition time in the respective imaging positions, as illustrated in FIG. 16A.

The control function 43a according to the fifth embodiment is capable of displaying a calculation result on the display 46, as illustrated in FIG. 16B, to present the calculation result to the operator. In the case of displaying the display information (FIG. 7) explained in the first embodiment and the display information illustrated in FIG. 16A, the scanogram is difficult to observe, because rectangles illustrating the imaging positions are superimposed on the scanogram. For this reason, as illustrated in FIG. 16B, the control function 43a displays arrows indicating the ranges and display information indicating the corresponding values of the gamma ray acquisition time, on the side of the scanogram. This display enables the operator to more easily observe the scanogram and the gamma ray acquisition time.

The first to the fifth embodiments described above illustrate the case of displaying the gamma ray acquisition time as the display information. However, embodiments are not limited thereto, but, display information including the couch moving speed may be displayed in the case where main imaging is executed by serial radiography.

The first to the fifth embodiments described above illustrate the calculating method of calculating values of the gamma ray acquisition time such that the product of the count value for each of the acquisition positions acquired in prior acquisition and the gamma ray acquisition time is fixed. However, embodiments are not limited thereto, but, for example, may have the structure of calculating the values of the gamma ray acquisition time for the respective imaging positions, based on a relational expression that is preset for the relation between the count value acquired in each of the acquisition positions in prior acquisition and the gamma ray acquisition time.

The first to the fifth embodiments described above illustrate the case of calculating values of the gamma ray acquisition time for the respective imaging positions in main imaging using the count values of gamma rays. However, embodiments are not limited thereto, but, for example, may have a structure of calculating the gamma ray acquisition time using the number of combinations of gamma rays counted simultaneously.

The first to the fifth embodiments described above illustrate the case of using a PET-CT apparatus. However, embodiments are not limited thereto, but may be applied to a PET apparatus, or a PET-MRI apparatus in which a PET apparatus and a magnetic resonance imaging (MRI) apparatus are integrated, as well as a PET-CT apparatus.

The control method explained in the first to the fifth embodiments is also applicable to a SPECT apparatus that reconstructs SPECT image data using counting information of gamma rays emitted by collapse events of radioactive isotopes specifically taken into the living tissue of the subject P. In addition, the calculating method explained in the first to the fifth embodiments is also applicable to a SPECT-CT apparatus in which a SPECT apparatus and an X-ray CT apparatus are integrated, or a SPECT-MRI apparatus in which a SPECT apparatus and an MRI apparatus are integrated.

The constituent elements of the devices illustrated in the first to the fifth embodiments are functional conceptual elements, and are not always required to be physically configured as illustrated. Specifically, the specific forms of distribution and integration of each of the devices are not limited to that illustrated, but the whole or part thereof may be functionally or physically distributed or integrated in a desired unit, according to various loads and the usage circumstances. In addition, the whole or part of each of the processing functions performed in the devices may be achieved with a CPU or a program that is analyzed and executed by the CPU, or may be achieved as hardware by a wired logic.

The control method explained in the first to the fifth embodiments may be achieved by executing a control program prepared in advance by a computer such as a personal computer and a workstation. The control program can be distributed through a network such as the Internet. The control program may be recorded on a computer-readable recording medium such as a hard disk, a flexible disk (FD), a CD-ROM, an NO, and a DVD, and may be executed by being read out of the recording medium with a computer.

At least one of the embodiments described above can improve the inspection efficiency.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine diagnostic apparatus comprising: processing circuitry configured to:
    perform control to execute gamma ray acquisition for main imaging for a subject, and prior acquisition to acquire gamma rays in a plurality of acquisition positions in the subject prior to the main imaging;
    calculate lengths of gamma ray acquisition time for respective imaging positions in the main imaging, based on count values of gamma rays acquired in the prior acquisition; and
    perform control to execute the main imaging, based on the calculated lengths of the gamma ray acquisition time for the respective imaging positions.

2. The nuclear medicine diagnostic apparatus according to claim 1, wherein the processing circuitry is configured to calculate the lengths of the gamma ray acquisition time for the respective imaging positions such that the count values of gamma rays in the respective imaging positions in the main imaging are substantially fixed, based on the count values of gamma rays in the acquisition positions acquired in the prior acquisition.

3. The nuclear medicine diagnostic apparatus according to claim 1, wherein the processing circuitry is configured to calculate the lengths of the gamma ray acquisition time for the respective imaging positions, based on count values of gamma rays acquired by simultaneous counting in the prior acquisition.

4. The nuclear medicine diagnostic apparatus according to claim 1, wherein the processing circuitry is configured to perform control to execute prior acquisition to acquire gamma rays in the acquisition positions that are intermittently set for a target area of the main imaging.

5. The nuclear medicine diagnostic apparatus according to claim 4, wherein the processing circuitry is configured to set a couch position such that a noted region is included in at least one acquisition position in the acquisition positions.

6. The nuclear medicine diagnostic apparatus according to claim 1, wherein the processing circuitry is configured to calculate the lengths of the gamma ray acquisition time for the respective imaging positions such that a product of the count value of gamma rays in each of the acquisition positions acquired in the prior acquisition and the value length of the gamma ray acquisition time in the imaging position corresponding to the acquisition position is substantially fixed.

7. The nuclear medicine diagnostic apparatus according to claim 1, wherein the processing circuitry is configured to calculate the lengths of the gamma ray acquisition time for the respective imaging positions such that the gamma ray acquisition time in the imaging position corresponding to the acquisition position having a minimum value of the count value of gamma rays acquired in the prior acquisition is equal to or smaller than a predetermined maximum acquisition time.

8. The nuclear medicine diagnostic apparatus according to claim 1, wherein the processing circuitry is configured to calculate the lengths of the gamma ray acquisition time for the respective imaging positions such that a sum of the lengths of the gamma ray acquisition time for the respective imaging positions is equal to or smaller than a predetermined total acquisition time.

9. The nuclear medicine diagnostic apparatus according to claim 1, wherein the processing circuitry is configured to calculate the lengths of the gamma ray acquisition time for the respective imaging positions such that the gamma ray acquisition time in the imaging position including a reference region is equal to or smaller than a predetermined reference acquisition time.

10. The nuclear medicine diagnostic apparatus according to claim 1, wherein the processing circuitry is configured to calculate the lengths of the gamma ray acquisition time for the respective imaging positions, based on a count value of gamma rays corresponding to an area excluding a certain region, in the count value of gamma rays acquired in the acquisition position including the certain region in the prior acquisition.

11. The nuclear medicine diagnostic apparatus according to claim 1, wherein the processing circuitry is configured to replace the length of the gamma ray acquisition time in the imaging position including a certain region, with a gamma ray acquisition time that is preset according to the certain region, in the lengths of the gamma ray acquisition time calculated for the respective imaging positions.

12. The nuclear medicine diagnostic apparatus according to claim 1, wherein the processing circuitry is configured to replace the length of the gamma ray acquisition time included in a predetermined numerical value range, with a gamma ray acquisition time that is preset according to the numerical value range, in the lengths of the gamma ray acquisition time calculated for the respective imaging positions.

13. The nuclear medicine diagnostic apparatus according to claim 12, wherein the processing circuitry is configured to set at least one of a numerical value range that is equal to or larger than a predetermined upper limit value, or a numerical value range that is equal to or smaller than a predetermined lower limit value, as the predetermined numerical value range.

14. The nuclear medicine diagnostic apparatus according to claim 1, wherein the processing circuitry is further configured to display a calculation result based on the count values of gamma rays acquired in the prior acquisition.

15. The nuclear medicine diagnostic apparatus according to claim 14, wherein the processing circuitry is configured to display the calculation result together with a scanogram.

16. A control method comprising:
performing control to execute gamma ray acquisition for main imaging for a subject, and prior acquisition to acquire gamma rays in a plurality of acquisition positions in the subject prior to the main imaging;
calculating lengths of gamma ray acquisition time for respective imaging positions in the main imaging, based on count values of gamma rays acquired in the prior acquisition; and
performing control to execute the main imaging, based on the calculated lengths of the gamma ray acquisition time for the respective imaging positions.

\* \* \* \* \*